United States Patent
Engstrand et al.

(10) Patent No.: US 10,898,332 B2
(45) Date of Patent: Jan. 26, 2021

(54) BONE IMPLANTS AND METHODS FOR CORRECTING BONE DEFECTS

(71) Applicant: OssDsign AB, Uppsala (SE)

(72) Inventors: Thomas Engstrand, Uppsala (SE); Håkan Engqvist, Uppsala (SE); Ghanim Ibrahim, Uppsala (SE); Jonas Åberg, Panama City (PA)

(73) Assignee: OSSDSIGN AB, Uppsala (SE)

( * ) Notice: Subject to any disclaimer, the term of this patent is extended or adjusted under 35 U.S.C. 154(b) by 0 days.

(21) Appl. No.: 15/778,856

(22) PCT Filed: Nov. 23, 2016

(86) PCT No.: PCT/IB2016/057076
§ 371 (c)(1),
(2) Date: May 24, 2018

(87) PCT Pub. No.: WO2017/089973
PCT Pub. Date: Jun. 1, 2017

(65) Prior Publication Data
US 2018/0344464 A1 Dec. 6, 2018

Related U.S. Application Data

(60) Provisional application No. 62/259,500, filed on Nov. 24, 2015.

(51) Int. Cl.
*A61F 2/28* (2006.01)
*A61B 17/80* (2006.01)
*A61F 2/30* (2006.01)

(52) U.S. Cl.
CPC ........ *A61F 2/2875* (2013.01); *A61B 17/8085* (2013.01); *A61F 2/28* (2013.01);
(Continued)

(58) Field of Classification Search
CPC ........ A61F 2/28; A61F 2/2803; A61F 2/2839; A61F 2/2835; A61F 2/2846;
(Continued)

(56) References Cited

U.S. PATENT DOCUMENTS

| 4,839,215 A | 6/1989 | Starling et al. |
|---|---|---|
| 4,905,679 A | 3/1990 | Morgan |

(Continued)

FOREIGN PATENT DOCUMENTS

| CN | 2607960 Y | 3/2004 |
|---|---|---|
| DE | 29913334 U1 | 9/1999 |

(Continued)

OTHER PUBLICATIONS

PCT/IB2016/057076, International Search Report, dated Jan. 19, 2017.
PCT/IB2016/057076, Written Opinion, dated Jan. 19, 2017.

*Primary Examiner* — Alvin J Stewart
(74) *Attorney, Agent, or Firm* — Porter Wright Morris & Arthur LLP

(57) ABSTRACT

A bone implant including a wire mesh support frame (120A) having a plurality of interconnected wire members and at least two fastening points in the form of retention eyelets (140A) connected to the support frame by deformable retention arms (138A), and a biocompatible plate (112) formed about the support frame, the plate having at least two open cavities (116) therein, wherein each of the retention arms extends out of the plate from or into one of the open cavities. A method for correcting a bone defect in a patient, a mesh support frame for use in a bone implant, and a method of fabricating a bone implant are also provided.

16 Claims, 26 Drawing Sheets

(52) U.S. Cl.
CPC ............... *A61F 2002/2835* (2013.01); *A61F 2002/2882* (2013.01); *A61F 2002/2885* (2013.01); *A61F 2002/2889* (2013.01); *A61F 2002/30578* (2013.01); *A61F 2002/30914* (2013.01)

(58) Field of Classification Search
CPC ........ A61F 2002/285; A61F 2002/2878; A61F 2/3099; A61F 2/3872; A61F 2/30734; A61F 2002/30736; A61F 2002/30751; A61F 2002/30754; A61F 2002/30756; A61F 2/46; A61F 2/4618; A61F 2/2875; A61F 2002/2882–2002/2889; A61F 2/30907; A61F 2002/30766; A61B 17/8085; A61B 17/8095
See application file for complete search history.

(56) References Cited

U.S. PATENT DOCUMENTS

| | | | |
|---|---|---|---|
| 5,139,497 A * | 8/1992 | Tilghman | A61B 17/8085 606/285 |
| 5,201,737 A | 4/1993 | Leibinger et al. | |
| 5,368,602 A | 11/1994 | De la Torre | |
| 5,372,598 A | 12/1994 | Luhr et al. | |
| 5,380,328 A | 1/1995 | Morgan | |
| 5,468,242 A | 11/1995 | Reisberg | |
| 5,503,164 A * | 4/1996 | Friedman | A61B 17/8085 128/897 |
| 5,545,226 A | 8/1996 | Wingo et al. | |
| 5,690,631 A | 11/1997 | Duncan et al. | |
| 5,743,913 A | 4/1998 | Wellisz | |
| 5,752,958 A | 5/1998 | Wellisz | |
| 5,766,176 A | 6/1998 | Duncan | |
| 5,769,637 A * | 6/1998 | Morgan | A61B 17/8071 433/176 |
| 5,785,712 A | 7/1998 | Runciman et al. | |
| 5,814,048 A | 9/1998 | Morgan | |
| 5,876,447 A | 3/1999 | Arnett | |
| 5,980,540 A | 11/1999 | Bruce | |
| 5,984,925 A | 11/1999 | Apgar | |
| 6,071,291 A * | 6/2000 | Forst | A61B 17/8085 606/151 |
| 6,093,188 A | 7/2000 | Murray | |
| 6,364,881 B1 | 4/2002 | Apgar et al. | |
| 6,521,246 B2 | 2/2003 | Sapieszko et al. | |
| 6,685,707 B2 | 2/2004 | Roman et al. | |
| 6,719,795 B1 | 4/2004 | Cornwall et al. | |
| 6,863,899 B2 | 3/2005 | Koblish et al. | |
| 6,905,516 B1 | 6/2005 | Lemaitre et al. | |
| 6,991,803 B2 | 1/2006 | Sapieszko et al. | |
| 7,118,705 B2 | 10/2006 | Lin | |
| 7,341,601 B2 | 3/2008 | Eisermann et al. | |
| 7,351,262 B2 | 4/2008 | Bindseil et al. | |
| 7,473,312 B2 | 1/2009 | Barralet et al. | |
| 7,501,018 B2 | 3/2009 | Engqvist et al. | |
| 7,625,399 B2 | 12/2009 | Case et al. | |
| 7,655,047 B2 | 2/2010 | Swords | |
| 7,682,400 B2 | 3/2010 | Zwirkoski | |
| 7,754,246 B2 | 7/2010 | Mosley et al. | |
| 7,833,253 B2 | 11/2010 | Ralph et al. | |
| 8,043,382 B2 | 10/2011 | Kumar et al. | |
| 8,231,624 B1 | 7/2012 | Strippgen | |
| 8,246,663 B2 | 8/2012 | Lovald et al. | |
| 8,281,638 B2 | 10/2012 | Metzger | |
| 8,287,915 B2 | 10/2012 | Clineff et al. | |
| 8,298,292 B2 | 10/2012 | Swords et al. | |
| 8,361,126 B2 | 1/2013 | Perrow et al. | |
| 8,366,751 B2 | 2/2013 | Pfefferle | |
| 8,398,720 B2 | 3/2013 | Swords | |
| 8,403,965 B2 | 3/2013 | Henderson et al. | |
| 8,435,265 B2 | 5/2013 | Konieczynski et al. | |
| 8,556,990 B2 | 10/2013 | Bartee et al. | |
| 8,795,377 B2 | 8/2014 | Engqvist et al. | |
| 8,906,074 B2 | 12/2014 | Kang et al. | |
| 9,023,085 B2 | 5/2015 | Strippgen | |
| 9,044,195 B2 * | 6/2015 | Manwaring | A61B 8/0808 |
| 9,220,597 B2 | 12/2015 | Engstrand et al. | |
| 9,445,900 B2 | 9/2016 | Engqvist et al. | |
| 9,517,097 B2 * | 12/2016 | Rise | A61B 17/8085 |
| 10,076,416 B2 * | 9/2018 | Engstrand | A61B 17/688 |
| 2004/0199250 A1 * | 10/2004 | Fell | A61F 2/30767 623/14.12 |
| 2005/0137699 A1 * | 6/2005 | Salahieh | A61F 2/2418 623/2.11 |
| 2005/0149032 A1 | 7/2005 | Vaughen et al. | |
| 2005/0216008 A1 | 9/2005 | Zwirnmann et al. | |
| 2005/0261780 A1 | 11/2005 | Heino et al. | |
| 2005/0288790 A1 | 12/2005 | Swords | |
| 2006/0116682 A1 * | 6/2006 | Longo | A61B 17/8061 606/280 |
| 2006/0224242 A1 * | 10/2006 | Swords | A61B 17/8085 623/17.19 |
| 2006/0235542 A1 | 10/2006 | Hodorek et al. | |
| 2006/0241592 A1 * | 10/2006 | Myerson | A61B 17/8061 606/280 |
| 2006/0271201 A1 | 11/2006 | Kumar et al. | |
| 2007/0112434 A1 | 5/2007 | Hakamatsuka et al. | |
| 2007/0156146 A1 * | 7/2007 | Metzger | A61B 17/8085 606/86 A |
| 2007/0173844 A1 | 7/2007 | Ralph et al. | |
| 2007/0233264 A1 | 10/2007 | Nycz et al. | |
| 2007/0233272 A1 | 10/2007 | Boyce et al. | |
| 2008/0009872 A1 | 1/2008 | Vaughen et al. | |
| 2008/0147098 A1 * | 6/2008 | Trieu | A61B 17/8085 606/151 |
| 2008/0147187 A1 * | 6/2008 | Bollinger | A61F 2/367 623/11.11 |
| 2008/0187571 A1 | 8/2008 | Clineff et al. | |
| 2008/0206300 A1 | 8/2008 | Bohner et al. | |
| 2009/0022771 A1 | 1/2009 | Lynn et al. | |
| 2009/0076605 A1 | 3/2009 | Linares et al. | |
| 2009/0076617 A1 | 3/2009 | Ralph et al. | |
| 2009/0099409 A1 | 4/2009 | Luehrs et al. | |
| 2009/0132047 A1 * | 5/2009 | Mansmann | A61F 2/0811 623/14.12 |
| 2009/0216338 A1 | 8/2009 | Gingras et al. | |
| 2009/0317447 A1 | 9/2009 | Levesque et al. | |
| 2010/0069455 A1 | 3/2010 | Takato et al. | |
| 2010/0069913 A1 | 3/2010 | Chirico et al. | |
| 2010/0094428 A1 | 4/2010 | Ralph et al. | |
| 2010/0324685 A1 * | 12/2010 | Castro | A61F 2/44 623/17.16 |
| 2011/0014244 A1 | 1/2011 | Sapieszko et al. | |
| 2011/0054540 A1 | 3/2011 | Ralph et al. | |
| 2011/0158963 A1 | 6/2011 | Font Perez et al. | |
| 2011/0218626 A1 | 9/2011 | Krinke et al. | |
| 2012/0058152 A1 | 3/2012 | Garcia de Castro Andrews et al. | |
| 2012/0165957 A1 | 6/2012 | Everland et al. | |
| 2012/0265312 A1 | 10/2012 | Burke et al. | |
| 2012/0271418 A1 | 10/2012 | Hollister et al. | |
| 2012/0289964 A1 | 11/2012 | Nakaji | |
| 2012/0310365 A1 * | 12/2012 | Chaput | A61F 2/30942 623/23.56 |
| 2012/0330435 A1 | 12/2012 | Engqvist et al. | |
| 2013/0012942 A1 | 1/2013 | Nelson et al. | |
| 2013/0053900 A1 | 2/2013 | Qwarnstrom et al. | |
| 2013/0066325 A1 | 3/2013 | Engqvist et al. | |
| 2013/0158670 A1 | 6/2013 | Tigno, Jr. | |
| 2013/0164707 A1 * | 6/2013 | Ali | A61C 8/0027 433/173 |
| 2013/0190873 A1 * | 7/2013 | Mansmann | A61F 2/3872 623/14.12 |
| 2013/0218282 A1 * | 8/2013 | Hunt | A61F 2/30 623/19.11 |
| 2014/0052264 A1 * | 2/2014 | Hufen | A61L 27/16 623/17.17 |
| 2014/0172116 A1 | 6/2014 | Maxson et al. | |
| 2014/0228960 A1 * | 8/2014 | Forterre | A61F 2/447 623/17.16 |
| 2014/0228969 A1 | 8/2014 | Engstrand et al. | |
| 2014/0243993 A1 | 8/2014 | Barrett et al. | |

(56) References Cited

U.S. PATENT DOCUMENTS

| | | | |
|---|---|---|---|
| 2014/0288650 A1 | 9/2014 | Hunt | |
| 2014/0316472 A1* | 10/2014 | Rise | A61B 17/8085 606/281 |
| 2015/0105806 A1* | 4/2015 | Dorafshr | A61F 2/2875 606/151 |
| 2015/0289979 A1* | 10/2015 | Gabele | A61L 27/446 623/23.55 |
| 2015/0374497 A1* | 12/2015 | Engstrand | A61F 2/2846 623/17.19 |
| 2016/0113770 A1* | 4/2016 | Early | A61B 17/8095 623/23.39 |
| 2017/0156770 A1* | 6/2017 | Stupak | A61B 17/8085 |
| 2017/0239054 A1* | 8/2017 | Engstrand | A61F 2/2875 |
| 2018/0221071 A1* | 8/2018 | Isch | A61F 2/446 |
| 2018/0221153 A1* | 8/2018 | Daniel | A61F 2/28 |
| 2018/0271659 A1 | 9/2018 | Mansmann et al. | |
| 2019/0133783 A1 | 5/2019 | Unger et al. | |
| 2019/0151113 A1* | 5/2019 | Sack | A61F 2/4455 |
| 2019/0240036 A1* | 8/2019 | Kowalczyk | A61F 2/4606 |

FOREIGN PATENT DOCUMENTS

| | | |
|---|---|---|
| EP | 544384 B1 | 1/1996 |
| EP | 433852 B1 | 3/1996 |
| EP | 1905368 A1 | 4/2008 |
| EP | 1420725 B1 | 8/2008 |
| EP | 1958580 A1 | 8/2008 |
| EP | 2014258 A1 | 1/2009 |
| EP | 2030596 A1 | 3/2009 |
| EP | 2474286 A1 | 7/2012 |
| JP | 2-143945 U | 12/1990 |
| WO | 03/007831 A1 | 1/2003 |
| WO | 2004/108019 A2 | 12/2004 |
| WO | 2008/002595 A2 | 1/2008 |
| WO | 2011/068451 A2 | 6/2011 |
| WO | 2011112145 A1 | 9/2011 |
| WO | 2012/016200 A1 | 2/2012 |
| WO | 2012/103164 A1 | 8/2012 |
| WO | 2012/118843 A1 | 9/2012 |
| WO | 2012/147114 A1 | 11/2012 |
| WO | 2014091469 A1 | 6/2014 |
| WO | 2014/125381 A2 | 8/2014 |
| WO | 2016/024248 A1 | 2/2016 |

* cited by examiner

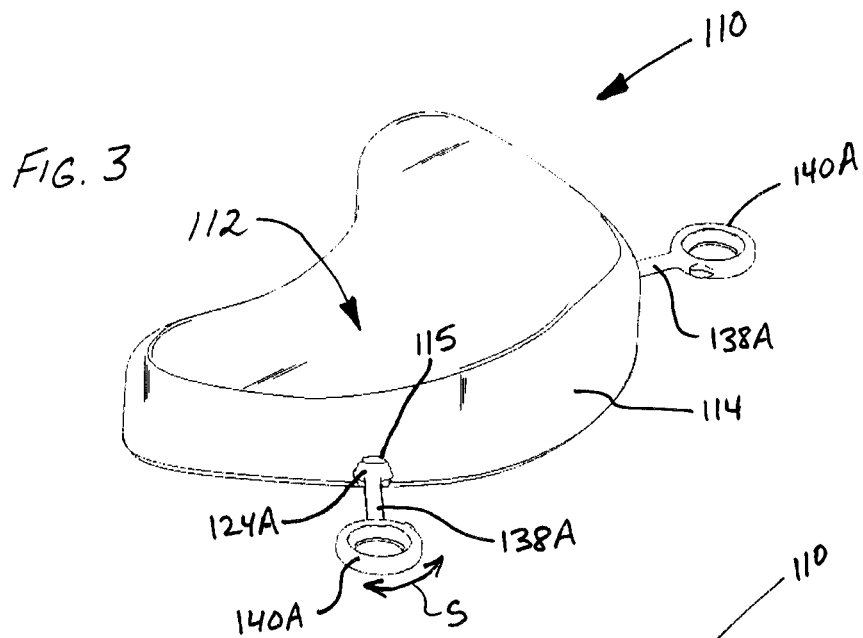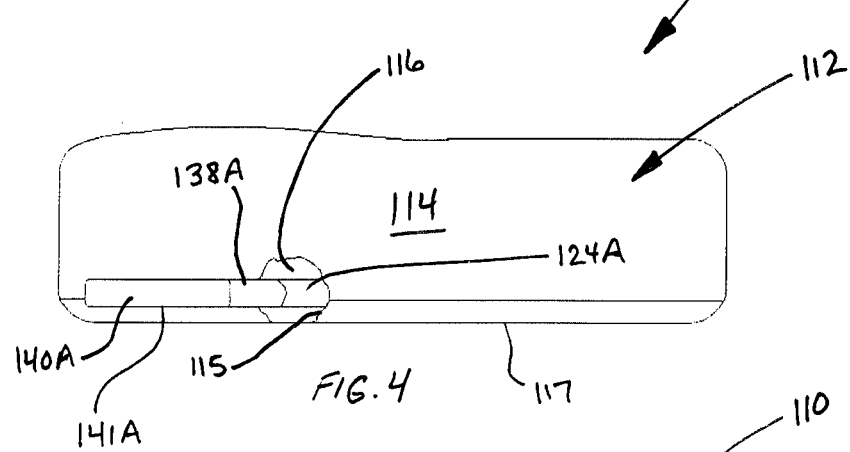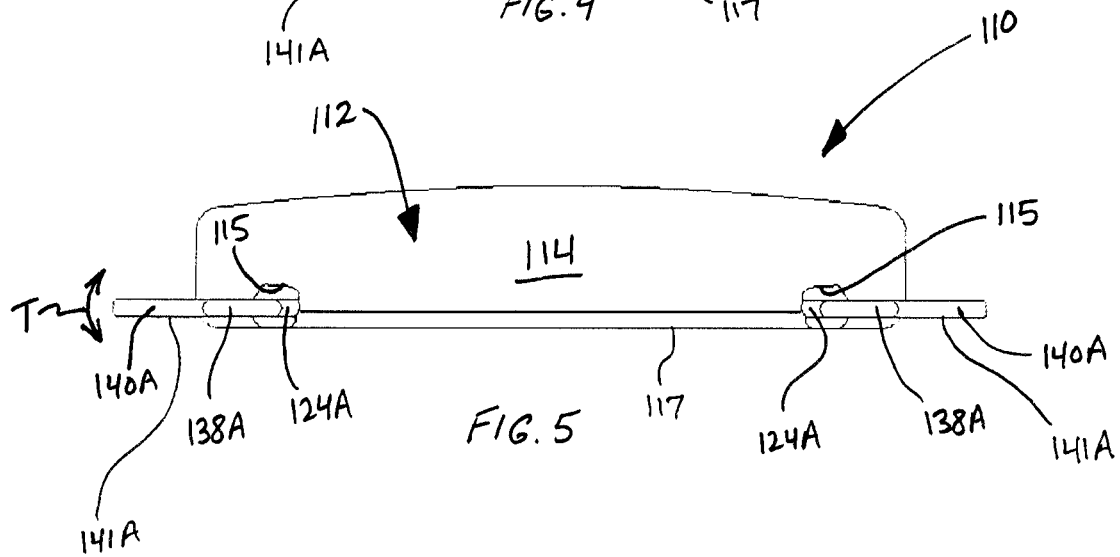

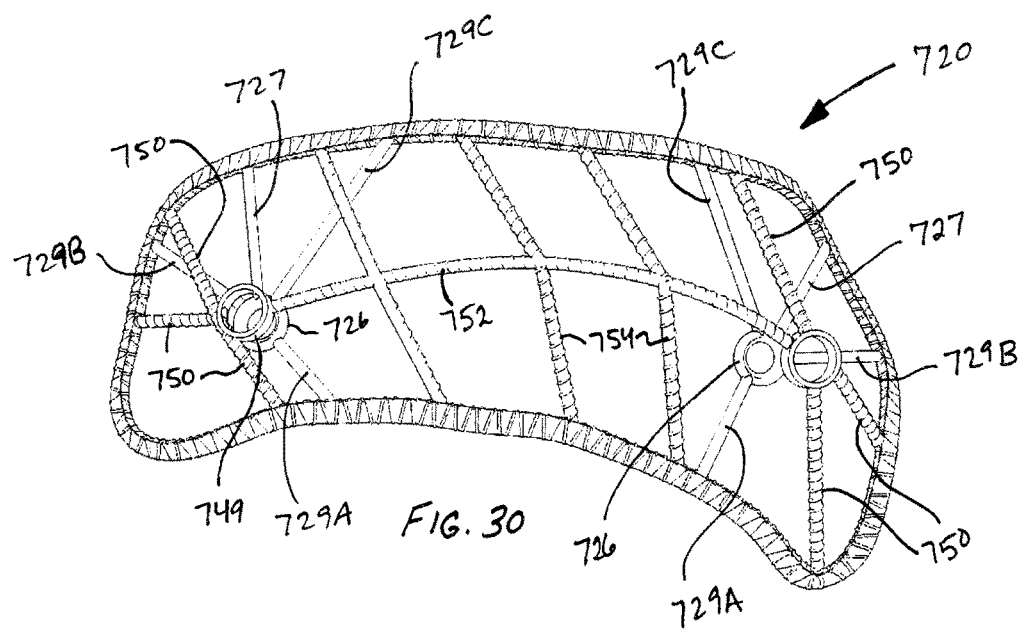
FIG. 30
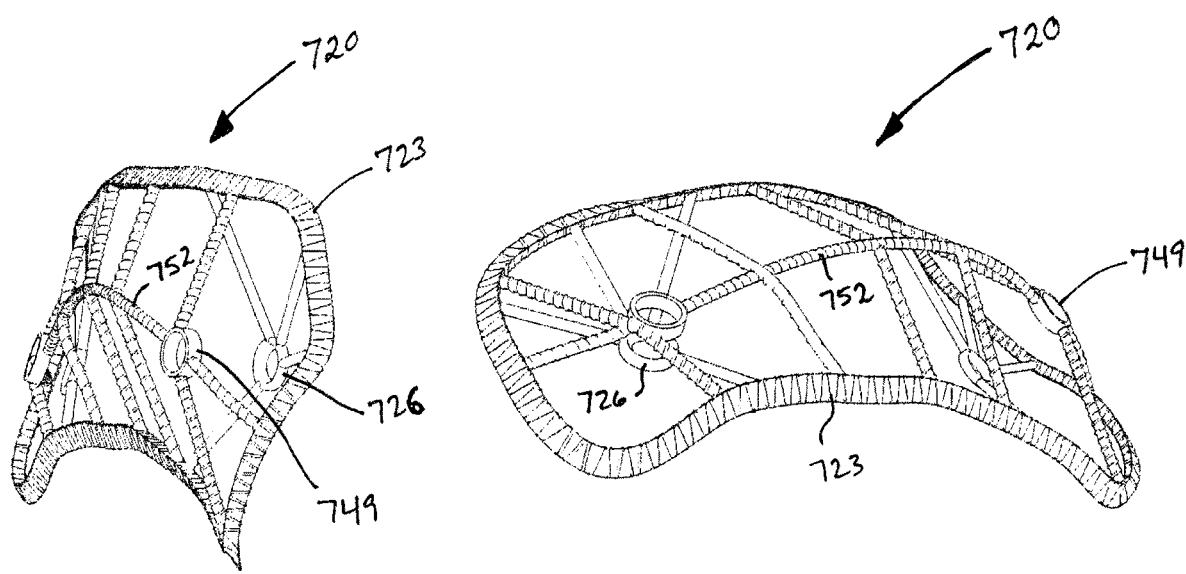
FIG. 31
FIG. 32

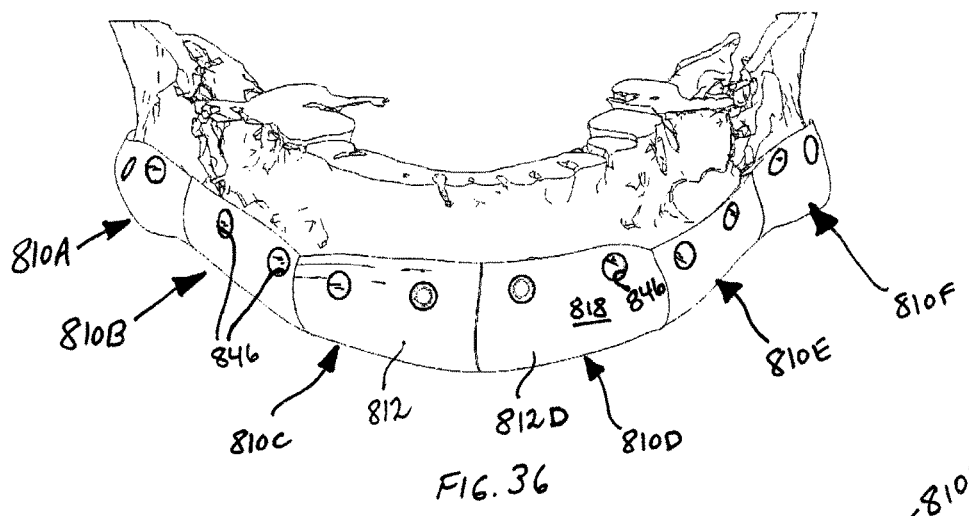
FIG. 36
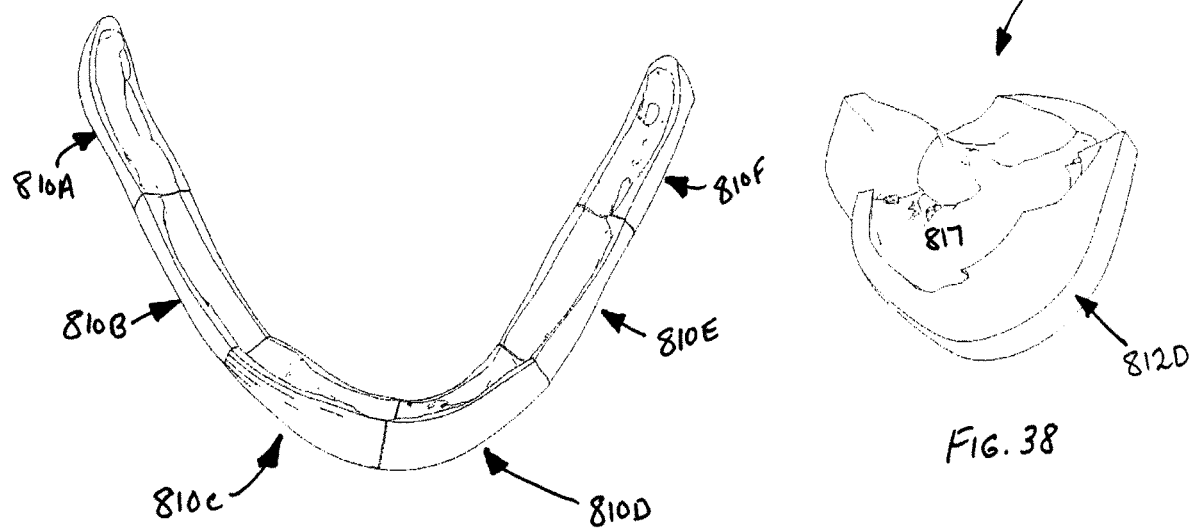
FIG. 37
FIG. 38

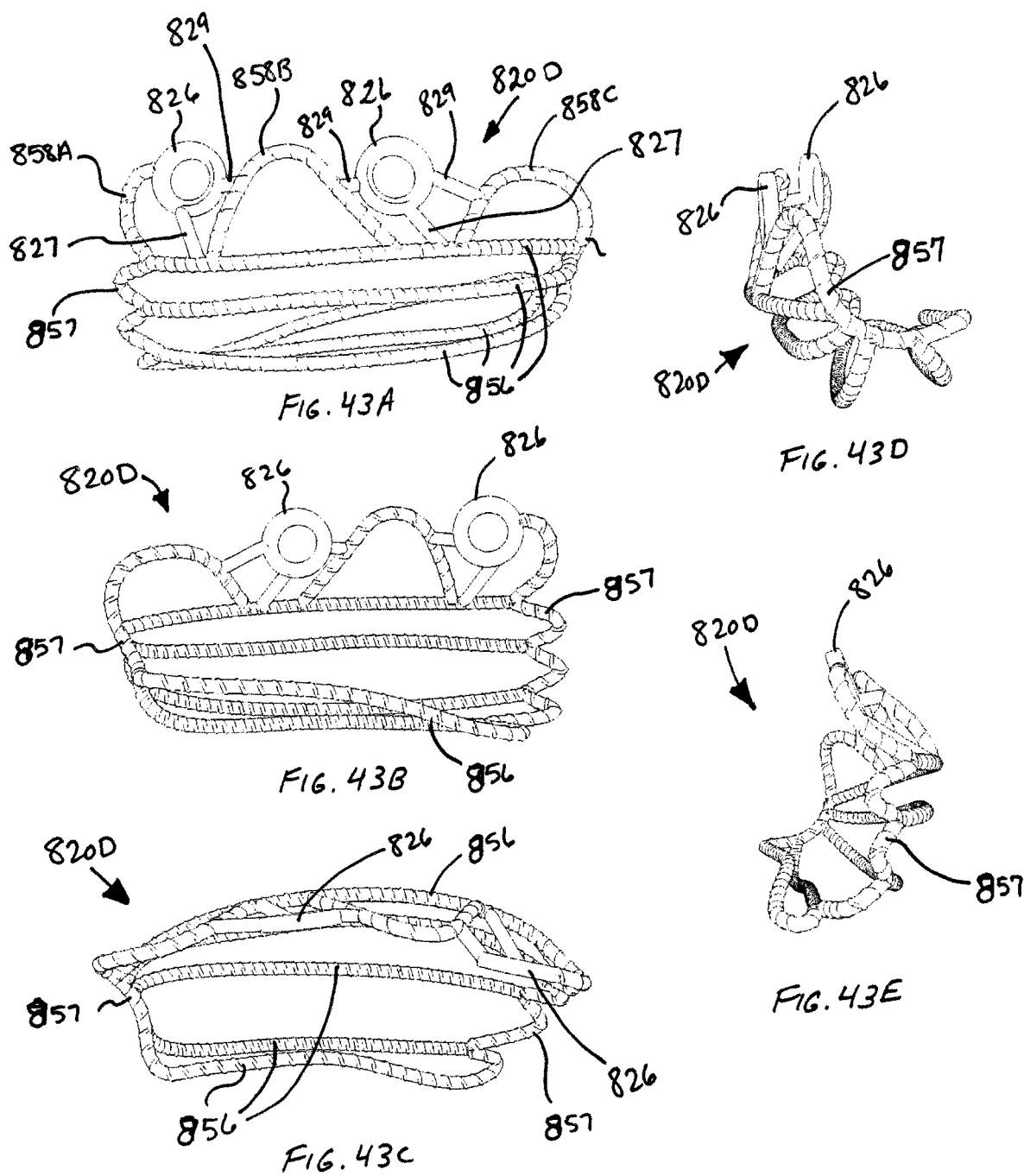

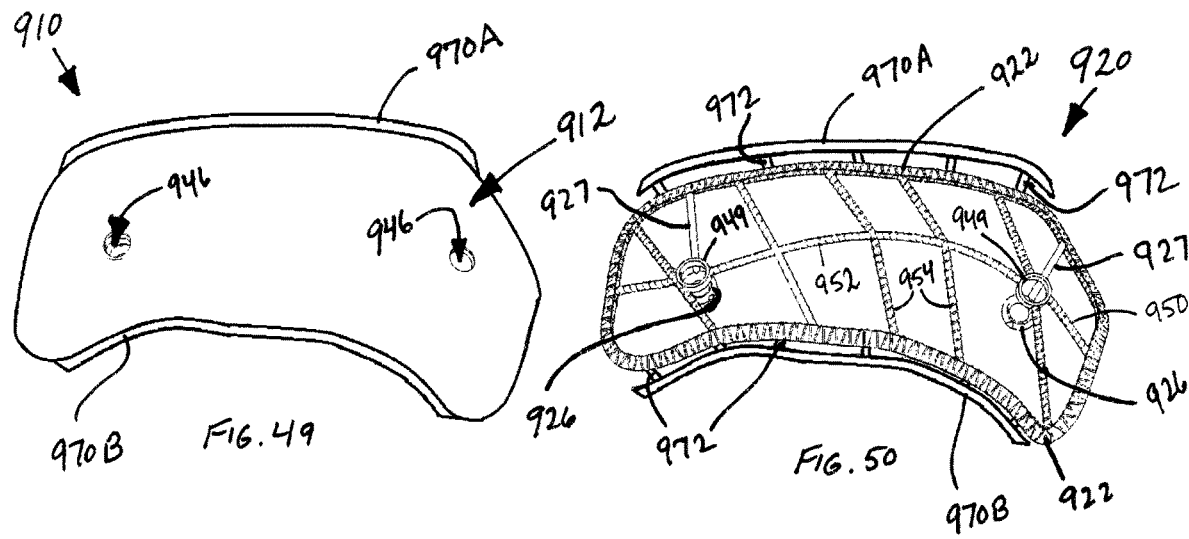
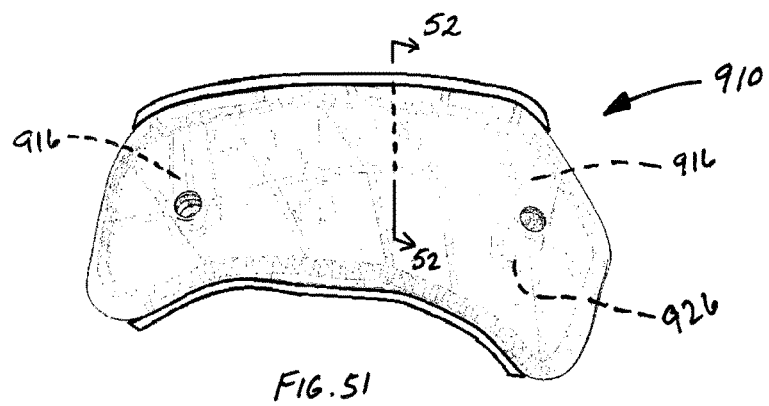
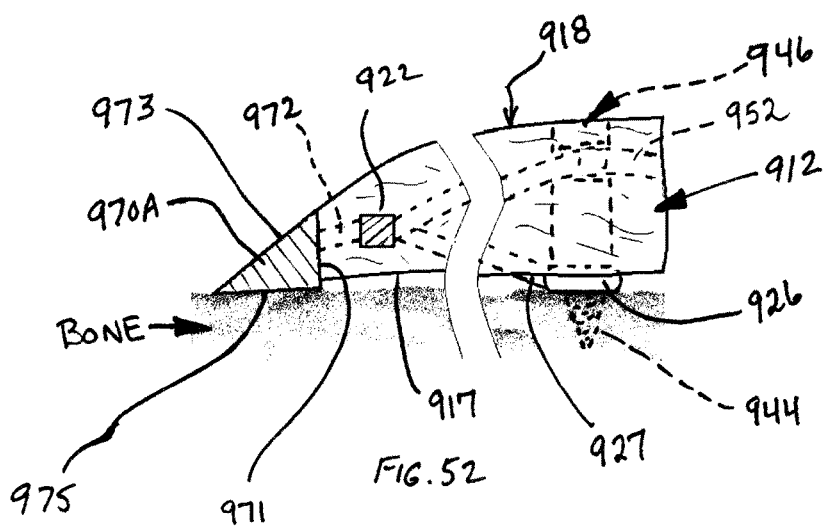

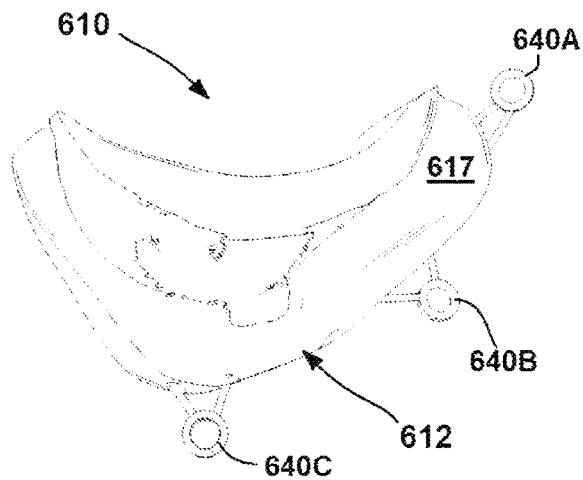
FIG. 55
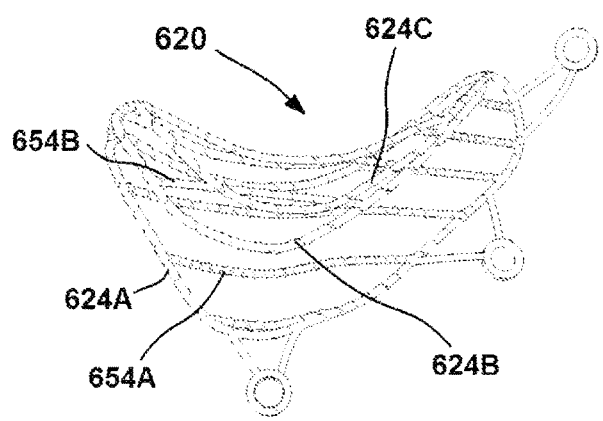
FIG. 56
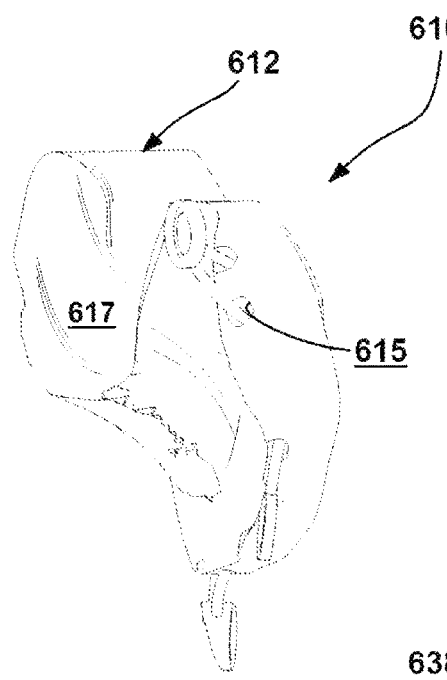
FIG. 57
FIG. 57A
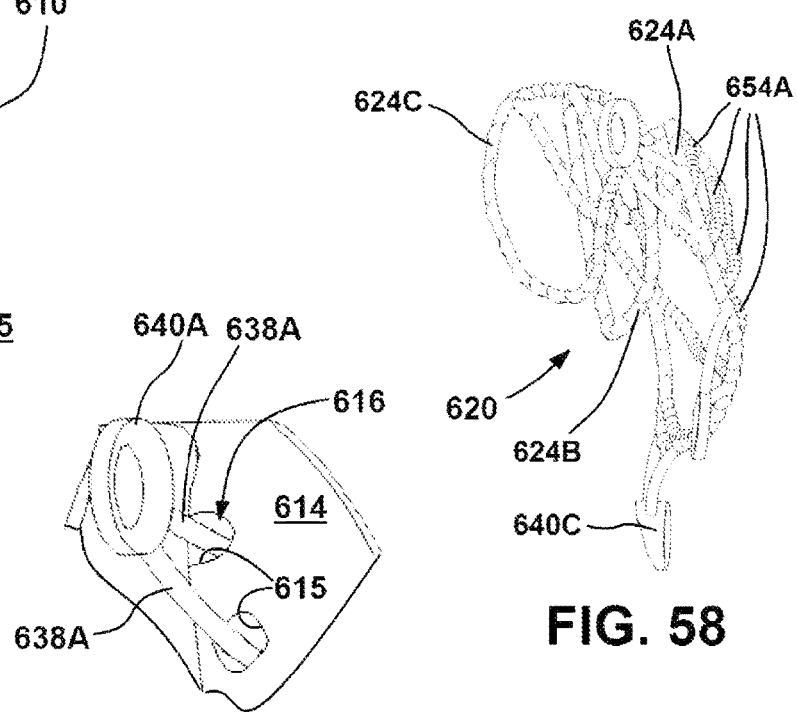
FIG. 58

BONE IMPLANTS AND METHODS FOR CORRECTING BONE DEFECTS

BACKGROUND

Bone tissue defects that cannot adequately heal via tissue regeneration often can be filled using autograph, allograph or synthetic materials that serve as a scaffold for new bone growth. For large defects such as defects in the cranium or long bones, however, such approaches are often not successful, and healing can be especially difficult. As a result, various alternative strategies have been developed which utilize metal meshes or various porous ceramic materials that provide structural support for new tissue (e.g., bone) growth. Many current strategies using metal mesh alone can be problematic due to low new bone formation and/or infections. Many currently used ceramic materials are mechanically weak and fragile, leading to a high risk of scaffold failure.

One advantage of metal meshes is that they often can be shaped to closely fit the defect. Ceramic implants, on the other hand, typically cannot be shaped after manufacturing and therefore have to be custom made in advance. In an attempt to overcome the problem of low bone in-growth with metal meshes, coating the mesh with hydroxyapatite powder has been proposed, particularly for use in revision surgery in joint replacement.

A more recent approach is described in PCT Pub. No. WO 2011/112145 A1, entitled Implants and Methods for Correcting Tissue Defects, published Sep. 15, 2011 (hereinafter, "the '145 App."). Further approaches are described in PCT Pub. No. WO 2014/125381 A2, entitled Mosaic Implants, Kits and Methods for Correcting Bone Defects, published Aug. 21, 2014 (hereinafter, "the '381 App."). The foregoing published applications are incorporated herein by way of reference. The '145 and '381 Apps. describe mosaic implants that comprise a plurality of biocompatible mosaic plates that are connected by a wire (e.g., wire mesh) anchoring arrangement.

While a variety of devices and techniques may exist for correcting bone defects, it is believed that no one prior to the inventors has made or used an invention as described herein.

BRIEF DESCRIPTION OF THE DRAWINGS

While the specification concludes with claims that particularly point out and distinctly claim the invention, it is believed the present invention will be better understood from the following description of certain examples taken in conjunction with the accompanying drawings. In the drawings, like numerals represent like elements throughout the several views.

FIGS. 3-5 are orthogonal, side elevational, and front elevational views, respectively, of the paranasal implant of FIG. 2, wherein the view shown in FIG. 5 is rotated 90° compared to that of FIG. 4.

FIG. 30 is the same view as FIG. 29, with the support frame shown prior to being modified for use in fabricating the implant of FIG. 24 (i.e., the retention eyelets are connected to the support frame by a plurality of retention arms).

FIGS. 31 and 32 are side and orthogonal views, respectively, of the unmodified support frame of FIG. 30.

FIG. 33 is the same view as FIG. 29, with guard assemblies positioned on the support frame of FIG. 29 prior to molding of the biocompatible plate over the support frame, while

FIGS. 35A-C depict the guard assembly used in FIGS. 33 and 34, wherein FIG. 35A is an upper elevational view of the guard assembly in unassembled form, FIG. 35B is a side view of the guard assembly in unassembled form, and FIG. 35C is an upper elevational view of the guard assembly in assembled form.

FIG. 36 is an enlarged view of a portion of FIG. 1, showing the six-section mandibular implant in greater detail.

FIG. 37 is a top view of the six-section mandibular implant of FIG. 36.

FIGS. 38 and 39 are side and front views, respectively, of one of the mandibular implant sections of FIG. 36.

FIGS. 41 and 42 are rear views of the mandibular implant section of FIG. 38, wherein FIG. 42 depicts the internal features of the support frame in hidden line.

FIGS. 43A-E are front, rear, top, right-side and left-side views, respectively, of the support frame used in the mandibular implant section of FIG. 38, with the support frame shown prior to being modified (i.e., the retention eyelets are connected to the support frame by a plurality of retention arms).

FIG. 49 is a view similar to FIG. 24, depicting an alternative embodiment of a supraorbital implant, while FIG. 50 depicts the support frame used in the implant of FIG. 49.

FIG. 51 is a top view of the implant of FIG. 49, wherein the plate is depicted translucently in order to better show the relationship between the biocompatible plate and the internal support frame.

FIG. 52 is a cross-sectional view of a portion of the implant of FIG. 49 taken along the line 52-52 thereof, wherein the implant is shown secured to bone in a patient.

FIG. 55 is a rear view of the zygoma implant of FIG. 53, and FIG. 56 is a rear view of the support frame of the zygoma implant of FIG. 53.

FIG. 57 is a rear side view of the zygoma implant of FIG. 53, FIG. 57A is an enlarged view of a portion of FIG. 57, and FIG. 58 is a rear side view of the support frame of the zygoma implant of FIG. 53.

DETAILED DESCRIPTION

Figure 1:
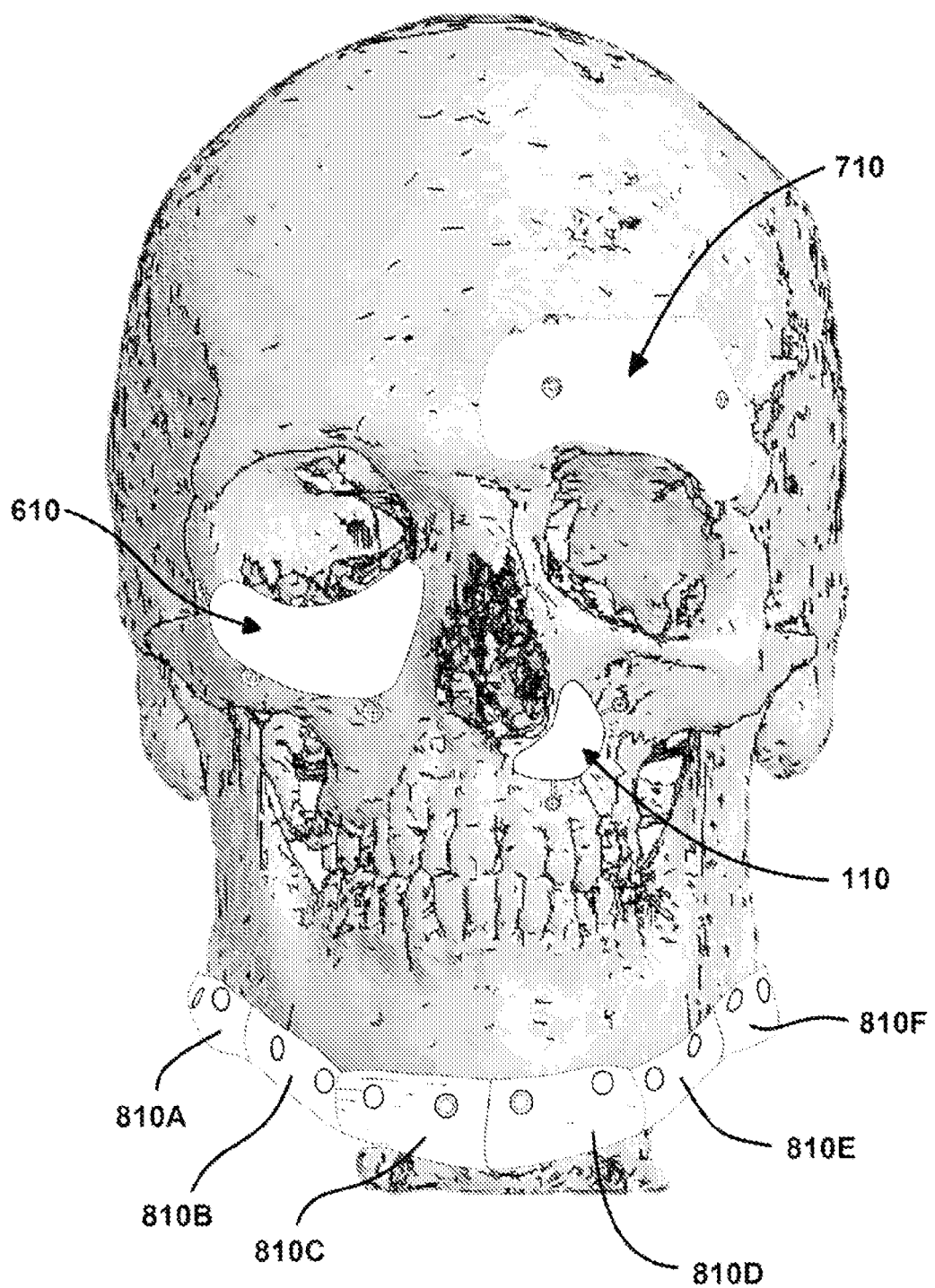
FIG. 1 schematically depicts a paranasal implant, a zygoma implant, a supraorbital implant, and a six-section mandibular implant implanted on a patient's skull.

The following description of certain examples should not be used to limit the scope of the present invention. Other features, aspects, and advantages of the versions disclosed herein will become apparent to those skilled in the art from the following description. As will be realized, the versions described herein are capable of other different and obvious aspects, all without departing from the invention. Accordingly, the drawings and descriptions should be regarded as illustrative in nature and not restrictive.

As used herein, the term "wire" refers to a strand, rod, strut, or similar structure having a length that is relatively long compared to its width and thickness, regardless of cross-sectional shape. For example, a "wire," as used herein, can have a circular, oval, rectangular, or other cross-sectional shape. In some of the embodiments described herein, one or more of the wires of the implants do not have a constant width and/or thickness along their entire length, and may have one or more segments or regions that are irregular in shape. For example, some wires may have a pleated or crimped segment that allows the effective length of the wire to be elongated or shortened, while others have segments of reduced width and/or thickness to provide regions of greater flexibility. In other embodiments, one or more wires have segments of increased width and/or thickness in order provide greater rigidity and/or support to the implant. An individual wire may be in the form of a single, continuous structure, or a plurality of individual filaments or strands may be combined to form a wire (e.g., wrapped or braided).

Examples described herein provide bone implants for correcting various bone defects, such as craniofacial implants for correcting bone defects of the skull (including the face and jaw). The implants described herein can also be used solely for cosmetic reasons—e.g., when a patient desires to enhance or otherwise modify a facial structure where there is no defect present.

In some embodiments, the implants comprise one or more biocompatible plates (e.g., hydraulic cement), each of which includes an internal support frame and one or more fastening points attached to the internal support frame. When the implant comprises two or more biocompatible plates, in some embodiments those plates are connected to one another, while in other embodiments they are not. The implants can be customized for each patient and the bone defect to be corrected, particularly with respect to the shape of the biocompatible plate(s) and the location of the fastening points. The location of the fastening points, for example, can be customized for each patent in order to ensure that fasteners used to affix the implant to surrounding bone will have sufficient and/or optimal purchase in the surrounding bone.

In general, embodiments of the bone implants described herein include a wire mesh support frame comprising a plurality of interconnected wire members, and a biocompatible plate formed (e.g., molded) about the support frame. The support frame includes at least two fastening points (e.g., retention eyelets) each of which is connected to the support frame by at least one deformable retention arm comprising one of the wire members of the support frame. The plate includes at least two open cavities therein (one for each fastening point retention arm). Each retention arm extends out of the plate either (a) from one of the open cavities, or (b) into one of the open cavities, such that the fastening points are located external to the plate for use in securing the implant to bone. In some instances the open cavities facilitate deformation (e.g., bending) of the retention arms with reduced risk of cracking the plate material. When the retention arms extend out of the plate from the open cavities, the fastening points (e.g., retention eyelets) are spaced away from the outer perimeter of the plate by the retention arms. In instances wherein the retention arms extend into the open cavities, the cavities are located within a bone-facing surface of the plate (i.e., the cavities extend inwardly from the bone-facing surface of the plate).

In some embodiments, a standardized internal support frame is physically manipulated and modified such as by bending, cutting and/or removing portions of the support frame so as to fit within, and adequately support a patient-customized biocompatible plate. After the support frame is modified, a patient-customized biocompatible plate is molded over the support frame. In other embodiments, a patient-customized internal support frame is created so as to fit within, and adequately support a patient-customized biocompatible plate designed for a particular patient and bone defect. By way of example, a digital representation of a patient-customized support frame is created. A patient-customized support frame is then fabricated based on its digital representation, such as by an additive manufacturing process (e.g., by selective laser melting) to produce the patient-customized support frame. Thereafter, the patient-customized biocompatible plate is molded over the support frame. While the implants described herein are typically configured for use in treating human patients, the implants can also be used in other mammals (with appropriate modifications for the particular mammal's anatomy).

In one particular embodiment, the implant comprises a paranasal implant comprising a biocompatible plate of customized shape and an internal support frame located within the plate. The internal support frame is formed using a standardized metal mesh arrangement having multiple options for customizing the mesh to fit within the plate so as to not only provide strength and support to the plate but also fastening points whose location is optimized for a particular patient. Portions of the metal mesh can be removed to ensure that the support frame fits within, yet adequately supports, the customized plate. Multiple fastening points are also provided on the support frame, allowing two or more of these fastening points to be selected for use, while the others fastening points are removed from the support frame prior to molding the plate about the support frame. Alternatively, one or more of the unused fastening points can remain on the support frame, particularly when they will be encased in the plate material or when they serve to provide alternative fastening locations for the surgeon to select at the time of surgery. While each such paranasal implant is molded using a patient-customized mold in which the support frame is positioned, this standardized support frame can be used to fabricate the metal mesh structure necessary for each particular implant.

Embodiments of the implants described herein also include fastening points such as one or more eyelets through which fasteners (e.g., bone screws) are driven into bone or other tissue at or surrounding an implantation site in order to secure the implant in place. In some instances, two or more eyelets are provided about the periphery of the implant. In other instances, the eyelets are located within the perimeter of the plate and the fasteners are inserted through bores extending through a thickness of the plate and through the eyelets into bone or other tissue at the implantation site. In some instances, a single retention eyelet (either an external or internal eyelet, as described further herein) can be employed. However, in general at least two retention eyelets are provided in order to ensure adequate fixation and mechanical stability of the implant, and to prevent rotation of the implant following implantation.

FIG. 1 depicts a variety of exemplary craniofacial implants implanted on a patient's skull. The implants include a paranasal implant (110), a zygoma implant (610), a supraorbital implant (710), and a six-section mandibular implant (810A-E). These implants are merely exemplary, as the structures, systems and methods described herein can be used to fabricate a wide variety of craniofacial implants for specific patients, for not only the repair or reconstruction of bone due to a congenital defect or trauma but also for purely cosmetic reasons. By way of example, the paranasal implant (110) can be used for patients having a cleft pallet.

Each of the depicted implants generally comprises a biocompatible plate (e.g., molded from a hydraulic cement), an internal support frame (e.g., formed of a metal such as titanium; not visible in FIG. 1), and one or more fastening points attached to the internal support frame. In the case of the paranasal implant (110), the fastening points comprise a pair of retention eyelets (140A) provided about the periphery of the implant. Bone screws (144) are inserted through the eyelets (140A) into bone adjacent the implantation site. Zygoma implant (610) is similarly configured, having three retention eyelets located about the periphery of the implant. The supraorbital implant (710) and the six-section mandibular implant (810A-E) (as well as alternative embodiments of the paranasal implant) have retention eyelets located within the perimeter of the plates, at the base of bores (746, 846, 946) that extend through the thickness of the cement plate. Fasteners (e.g., bone screws) are inserted into the bores and through the eyelets into bone at the implantation site.

In further alternative embodiments, the implant comprises both internal and external retention eyelets. For example, the implant can include external retention eyelets such as those provided on the paranasal or zygoma implants (110, 610)), as well as internal eyelets and associated bores such as those provided on supraorbital implant (710). All of these retention eyelets can be used for securing the implant in place, or the surgeon can select which ones to use at the time of surgery (and, optionally, removing any external retention eyelets that are not used along with the external portions of their retention arms).

The internal support frame can be made from any of a variety of biocompatible materials suitable for implantation in a patient, such as various metals, polymers, or even composite materials of two or more metals and/or polymers. Non-limiting examples include biocompatible polymers such as polycaprolactone, shape memory alloys such as nitinol, and metals (including alloys) such as titanium, titanium alloys (e.g. Ti-6A1-4V) and stainless steel. The support frame can also be formed in any of a variety of manners such as forging, casting, molding, extrusion, cutting, etching, stamping, and additive manufacturing techniques such as selective laser melting or selective laser sintering).

The biocompatible plates can be composed of any of a variety of resorbable and/or stable (i.e., non-resorbable) biocompatible materials, including various types and/or combinations of polymers, ceramics and metals. In some embodiments, the plates are composed of an osteoconductive and/or osteoinductive material. Osteoconductive materials serve as a scaffold on which bone cells will attach, migrate, and grow and divide so as to form new bone on the surfaces of the plates. Osteoinductive materials induce new bone formation around the plates.

In some embodiments, the biocompatible plate is composed of a moldable bioceramic or biopolymer material. While bioceramic materials can be produced by sintering ceramic powders, it can be difficult to produce complex shapes in this manner. Alternatively, bioceramics can be formed by a chemical bonding route whereby the ceramic material is formed by chemical reaction, such as a cement setting and hardening reaction.

In some embodiments, a bioceramic material comprising an hydraulic cement composition is used to mold the biocompatible plate. Non-limiting examples include cement precursor compositions comprising one or more Ca-salts such as calcium sulfates, calcium phosphates, calcium silicates, calcium carbonates and combinations thereof. As further described herein, the biocompatible plate is formed by molding the cement composition around portions of the support frame. For example, a powdered cement precursor composition is combined with either a non-aqueous water-miscible liquid or a mixture of water and a non-aqueous water-miscible liquid. The mixture is then poured or injected into a mold having the support frame positioned therein, and allowed to harden (e.g., in a water-containing bath) so as to form the plate about the support frame.

Various cement compositions that may be used to mold the plates are described, for example, in PCT Pub. No. WO 2014/091469 A1, published Jun. 19, 2014, titled "Cement-Forming Compositions, Monetite Cements, Implants and Methods for Correcting Bone Defects." Alternative cement compositions for use in molding the plates, including storage stable premixed hydraulic cement compositions, are described in PCT Pub. No. WO 2013/035083 A2, published Mar. 14, 2013, titled "Storage Stable Premixed Hydraulic Cement Compositions, Cements, Methods, and Articles." Still further cement compositions which may be used to mold the plates are described, for example, in the '145 App., as well as PCT Pub. No. WO 2013/027175 A2, published Feb. 28, 2013, titled "Implants and Methods for Using the Implants to Fill Holes in Bone Tissue," and PCT Pub. No. WO 2010/055483 A2, published May 20, 2010, titled "Hydraulic Cements, Methods and Products." Each of the foregoing patent applications and publications is incorporated by reference herein.

In one embodiment, the composition used to mold the plate is a calcium phosphate cement-forming composition that comprises a monetite-forming calcium-based precursor powder combined with a non-aqueous water-miscible liquid. In one specific embodiment, the monetite-forming calcium-based precursor powder comprises monocalcium phosphate (monocalcium phosphate monohydrate (MCPM) and/or anhydrous monocalcium phosphate (MCPA)) and β-tricalcium phosphate in a weight ratio of 40:60 to 60:40, and from 2 to 30 weight percent, based on the weight of the precursor powder, of dicalcium pyrophosphate powder (also referred to herein as calcium pyrophosphate). The powder to liquid (wt/vol) ratio in the composition is from 2 to 6 g/ml.

In another embodiment, the composition used to mold the plate is a calcium phosphate cement-forming composition that comprises a monetite-forming calcium-based precursor powder that is adapted to be mixed with an aqueous liquid or exposed to an aqueous liquid to achieve hardening. In one specific embodiment, the monetite-forming calcium-based precursor powder comprises monocalcium phosphate (monocalcium phosphate monohydrate (MCPM) and/or anhydrous monocalcium phosphate (MCPA)) and β-tricalcium phosphate in a weight ratio of 40:60 to 60:40, and from 2 to 30 weight percent, based on the weight of the precursor powder, of dicalcium pyrophosphate powder (also referred to herein as calcium pyrophosphate).

The porosity of the molded plate can also be controlled, as the porosity affects bone in-growth and the resorption time in vivo. For example, porosity may be controlled by controlling monocalcium phosphate particle size in the precursor composition, and/or adding one or more porogens to the precursor composition. In some embodiments where porosity is desired, the molded plate has a porosity of from 40 to 50%, while in other embodiments, the porosity is about 46%.

In one specific embodiment, the monetite-forming calcium-based precursor powder mixture is mixed with a non-aqueous water-miscible liquid such as glycerol, optionally including up to 20% water (based on the total liquid volume). After mixing, the cement precursor mixture is poured or injected into a mold having the support frame positioned therein. The filled mold is then exposed to water, such as by placing the mold in a water bath, and the cement is allowed to harden (e.g., about 24 hours in a room temperature water bath). After the cement has hardened, the implant is removed from the mold. Further processing such as soaking the implant in water to remove glycerol residue may be performed, as necessary.

The thus-formed plate of the implant in the example described above will comprise monetite ($CaHPO_4$) and 2-30 wt. % dicalcium pyrophosphate, along with varying amounts of other materials such as β-tricalcium phosphate and minor amounts of brushite ($CaHPO_4.2H_2O$) (e.g., less than 2 wt. % or less than 1 wt. %). The plate in some embodiments comprise at least 65 wt %, at least 70%, at least 75%, at least 80%, at least 85%, or at least 90% monetite. The presence of dicalcium pyrophosphate not only delays resorption of the plate but also provides osteoinductivity (i.e., promotes new bone growth around and between the plate as compared to similar monetite formulations which do not include dicalcium pyrophosphate).

In yet another embodiment, the plates are formed of a hardened monetite cement comprising at least 70 wt. % monetite and from 3 to 30 wt. % dicalcium pyrophosphate, or, more specifically, comprising at least 80 wt. % monetite and from 3 to 20 wt. % dicalcium pyrophosphate. The hardened monetite cement may further comprise β-tricalcium phosphate (β-TCP). In a further specific embodiment, the hardened monetite cement comprises at least 75 wt. % monetite, from 3 to 20 wt. % dicalcium pyrophosphate, and from 1 to 15 wt. % β-TCP; or, at least 80 wt. % monetite, from 3 to 15 wt. % dicalcium pyrophosphate, and from 1 to 10 wt. % β-TCP. In more specific embodiments, the dicalcium pyrophosphate is β-dicalcium pyrophosphate. In yet additional embodiments, the hardened monetite cement is formed from a monetite-forming precursor powder comprising monocalcium phosphate, β-TCP, and from 3 to 30 wt. %, or from 3 to 20 wt. % (based on the total weight of the precursor powder) dicalcium pyrophosphate. In specific embodiments, the weight ratio of monocalcium phosphate to β-TCP in the precursor powder is in a range of 40:60 to 60:40, or, more specifically, in a range of 45:55 to 52:48. In additional specific embodiments, the monocalcium phosphate is monocalcium phosphate monohydrate.

In still further embodiments, the plates are formed of a hardened apatite cement comprising from 1 to 30 wt. % dicalcium pyrophosphate. In more specific embodiments, the hardened apatite cement comprises greater than 80 wt. % apatite. The hardened apatite cement may further comprise β-tricalcium phosphate (β-TCP). In specific embodiments, the hardened apatite cement comprises greater than 80 wt. % apatite, 1 to 15 wt. % β-tricalcium phosphate, and 1 to 15 wt. % β-dicalcium pyrophosphate. In more specific embodiments, the dicalcium pyrophosphate is β-dicalcium pyrophosphate. In yet additional embodiments, the hardened apatite cement is formed from a calcium phosphate cement-forming composition comprising an apatite-forming calcium-based precursor powder comprising α-tricalcium phosphate and/or tetracalcium phosphate, and from 1 to 30 wt. %, based on the total weight of the precursor powder, of dicalcium pyrophosphate powder.

Figure 2:
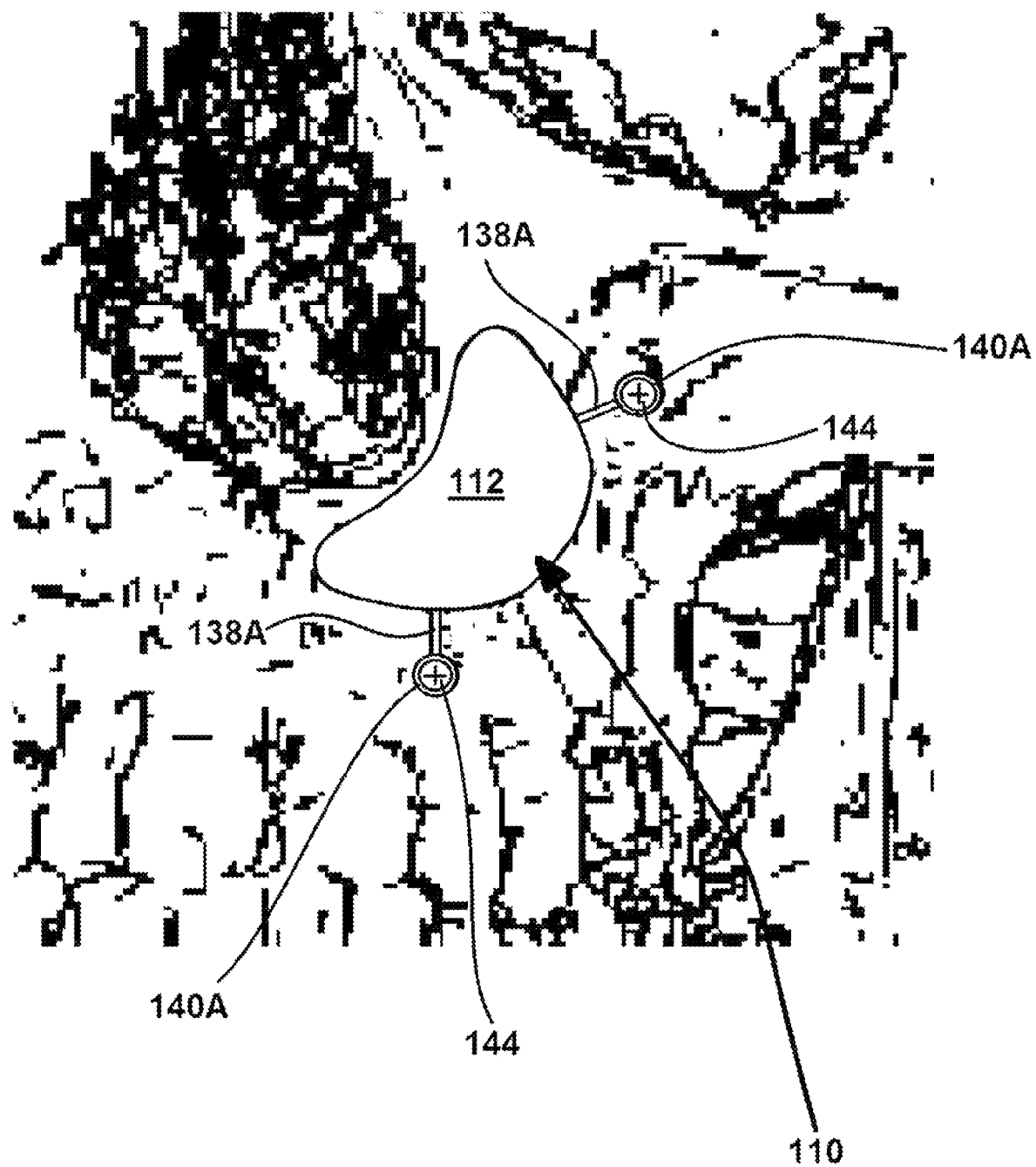
FIG. 2 is an enlarged view of a portion of FIG. 1, showing the paranasal implant in greater detail.

Looking first at the paranasal implant depicted in FIGS. 1-5, paranasal implant (110) comprises a biocompatible plate (112) that is adapted to be secured to, for example, a patient's maxilla bone. As seen in FIGS. 1 and 2, the paranasal implant (110) is secured to surrounding bone using fasteners such as bone screws (144) driven through a pair of fastening points in the form of retention eyelets (140A). When used in other locations, the implant (110) can be secured to other craniofacial bones such as the mandible, frontal, nasal and/or zygomatic bones.

Each retention eyelet (140A) is provided at the external end of a retention arm (138A) that extends out of the outer sidewall (114) of the plate (112) through an aperture (115), as further described below. As best seen in FIG. 3, the retention eyelets (140A) are countersunk such that the head of a screw inserted therethrough will not extend above the upper surface of the retention eyelet (140A). In alternative embodiments the eyelets are not countersunk.

The implant (110) includes an internal wire mesh support frame (120A), with the plate (112) molded about the support frame. Any of the previously described materials and compositions can be used to mold the plate (112) about the support frame (120A), such as a monetite-forming, hydraulic cement composition. If desired, the implant (110) can be customized based on the needs of a particular patient, particularly the size and configuration of the biocompatible plate (112) and the location of the retention eyelets (140A). However, even if a standardized implant (110) (including a standardized implant selected from a plurality of standardized implants of varying size and/or configuration) is used, the location of the retention eyelets (140A) can be adjusted at the time of implantation, as further described herein. It will therefore be understood that the particular implant (110), including the plate (112) and modified support frame (120A) shown in FIGS. 1-10, is merely exemplary.

The internal, wire mesh support frame used in the exemplary paranasal implant (110) can be custom-fabricated from scratch for each patient (e.g., by selective laser melting) so as to not only fit within and adequately support a patient-customized biocompatible plate (112), but also to locate the retention eyelets at an appropriate location for securing the implant in place. Alternatively, and as depicted in FIGS. 6-10, internal support frame (120A) is fabricated from a standardized support frame (120) (depicted in FIGS. 11-16). Once the desired size and shape of the plate (112) is determined, along with the desired location of the retention eyelets, the standardized support frame (120) shown in FIGS. 11-16 is physically modified by bending, cutting and/or removing portions of the support frame so that the support frame not only fits within and adequately supports the plate (112), but also to locate the retention eyelets (140A) at an appropriate location for securing the implant in place. The modified support frame (120A) is then positioned within a customized mold for the plate (112), and the plate is molded about the support frame such that the retention arms (138A) and retention eyelets (140A) are not covered by cement (or other biocompatible plate material). This allows the retention arms (138A) to be deformed (e.g., bent, including twisted and/or flexed) by the surgeon at the time of implantation in the patient so as to ensure proper positioning and adequate securement of the implant (110). Thus, while each paranasal implant (110) is molded using a patient-customized mold in which the modified support frame (120A) is positioned, a standardized support frame (120) can be used to fabricate the metal mesh structure necessary for each particular implant. The exemplary paranasal implant (110) and its modified support frame (120A) will be described first, followed by a description of the standardized support frame (120) from which the modified support frame is fabricated.

As seen in FIGS. 3-5, retention arms (138A) are affixed to and extend away from a rim (124A) located within the plate (112). The rim (124A) is part of the modified mesh support frame (120A), and is described in more detail below. While implant (110) is custom fabricated to meet the needs of a particular patient, including deforming portions of the support frame (120A) prior to molding the plate about the support frame, the retention arms (138A) also can be deformed (e.g., bent, including twisted and/or flexed) at the time of implantation in order to ensure a proper fit. For example, the retention arms (138A) can be deformed by twisting or otherwise bending the retention arms so that the bottom surface (141A) of the retention eyelets (140A) will lie flush (or nearly flush) against the surface of the bone into which the bone screws are to be inserted.

In order to reduce the risk of cracking of the plate (112) when the retention arms (138A) are deformed at the time of implantation, the plate (112) is molded about the mesh support frame such that retention arms (138A) as well as a portion of the outer rim (124A) adjacent the retention arms (138A) is not covered by the plate material (e.g., cement). Thus, not only do the retention arms (138A) extend out of the plate (112) through an aperture (115) that is larger in diameter than that of the retention arms (138A), the retention arms also extend out of the plate from open internal cavities (116) provided in the plate material adjacent each aperture (115). In other words, each internal cavity (116) extends inwardly into the plate material from an aperture (115), wherein both the aperture (115) and the cavity (116) are larger in diameter than the retention arm (138A) extending therefrom, such that the retention arm (138A) is not in contact with (or has only minimal contact with) the plate material. By providing such internal cavities (116) and oversized apertures (115), retention arms (138A) can be bent considerably without risk of cracking the plate material. For example, retention arms (138A) can be bent not only side-to-side (arrow S in FIG. 3), but also up and down (arrow T in FIG. 5) or even twisted.

Although each paranasal implant (110) can be custom-fabricated for individual patients, as best seen in FIGS. 4 and 5 the apertures (115) through which the retention arms (138A) extend are generally located adjacent the bottom surface (117) (the bone-facing surface) of the plate (112) (at least in the particular embodiment shown in FIGS. 1-10). Thus, in the particular embodiment shown, each aperture (115) is within the lower third of the outer periphery of the plate (112) (when viewed from the side, as in FIGS. 4 and 5). While the apertures (115) can be circular in shape, and the associated cavity cylindrical in shape, any of a variety of shapes can be employed. Thus, the apertures can be circular, semi-circular, oval, semi-oval, ovoid, semi-ovoidal, elliptical, semi-elliptical, polygonal or irregular in shape, and the cavities can similarly have any of these same cross-sectional shapes. If desired, the cavities (116) can also taper inwardly. In the example shown, and as best seen in FIG. 10A, cavity (116) is open at its bottom (i.e., in the bone-facing surface (117) of the plate) and aperture (115) is therefore semi-circular in shape. This arrangement allows for greater downward deformation of the retention arm (138A). The outer rim (124A) shown in the embodiment of FIG. 10A is also textured rather than smooth, as further described herein with reference to the implant (710), thereby improving cement adherence to support frame and preventing fracturing of the cement along a fracture surface. It will be understood that such texturing can be provided on the other surfaces of the support frame 120A located within the plate.

As also seen in FIG. 10A, the outer rim (124A) extends across the interior of the cavity (116). In this instance, the cavity is sufficiently deep so that the entire circumference of the outer rim (124A) is located within the cavity (116). Alternatively, the cavity can be configured such that less than the entire circumference of the outer rim (124A) is located in the cavity. The size of the aperture (115) and cavity (116), as well as the distance between the outer rim (124A) (or other portion of the support frame to which the retention arm is attached) are chosen in order to allow for the desired amount of retention arm deformation the retention arm contacts the plate. For example, in some embodiments, the cavity and aperture are configured to permit a retention arm bending angle of up to 70° (see FIG. 10A), or up to about 45°. In general, the retention arm will tend to bend more adjacent its connection to the support rim, resulting in a slightly curved retention arm following bending. Thus, as used herein and as depicted in FIG. 10A, the bending angle is defined based on an imaginary line extending between (i) the center of the connection point of the retention arm to the support rim, and (ii) the center of the retention eyelet. With respect to vertical deformation of the retention arm (138A) in the exemplary embodiment shown, since the bottom of the cavity (116) is open, the permitted bending angle of the retention arm in the downward direction is not limited by the size of the cavity or aperture (115). It will also be understood that the permitted bending angles may not be the same in all direction, particular if, for example, the aperture (115) is semi-oval or other non-semicircular shape.

In the example shown, in order to provide the desired permitted bending angle, the distance (L2) between the retention arm and the wall of the cavity (116) and aperture (115) is between about 0.5 and about 2.5 mm, or between about 1 and about 2 mm. The distance (L1) between the rim (124A) and the outer perimeter of the plate is less than about 2 mm, or about 1 mm. Similar sizes and spacings, as well as permitted bending angles, can be employed with any of the other implants described herein that employ external retention eyelets. Of course the dimensions and spacings necessary to provide the desired permitted bending angles will depend, in part, on the diameter of the retention arms. In some embodiments sufficient permitted bending angles are obtained when the diameter of the aperture is at least 1.5 times, at least two times, or in some instances at least three times, the outer diameter of the retention arm.

In addition, plate (112) and support frame (120A), when viewed from the top, are generally kidney-shaped, although once again this is merely exemplary of one possible shape. In addition, the kidney-shape of the standardized support frame (120) from which support frame (120A) is fabricated advantageously provides a wide variety of options for modifying the support frame to fit within a variety of plate shapes, sizes and configurations.

Figure 6:
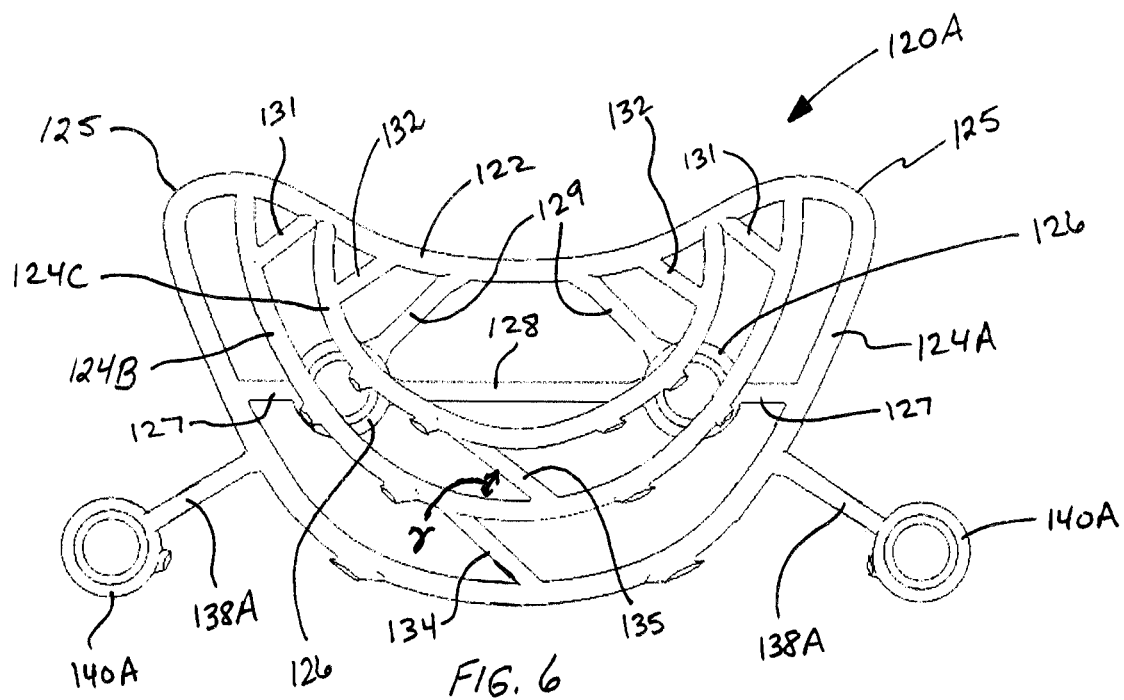
FIGS. 6 and 7 are top plan and orthogonal views, respectively, of the support frame used in the paranasal implant of FIGS. 2-5.
Figure 7:
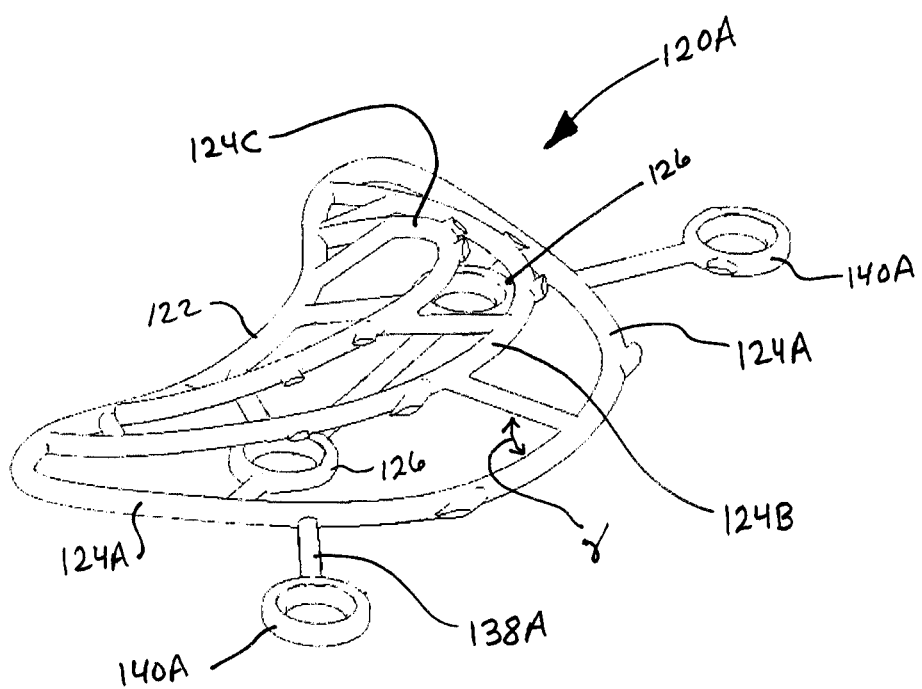

Wire mesh support frame (120A) is depicted in FIGS. 6 and 7, and includes a first rim traversing a continuous, closed loop defined by a concavely curved inner wire rim (122) and a convexly curved first outer wire rim (124A). Inner rim (122) and first outer rim (124A) generally lie in the same plane (the "base plane" of the support frame) and meet at their respective ends so as to form a kidney shape having outer curved corners (125) (when viewed from the top, as in FIG. 6). A pair of interior eyelets (126) is located between the inner rim (122) and first outer rim (124A), and is coplanar therewith. Interior eyelets (126) provide additional strength and rigidity to the support frame (120A) within the plate (112). In addition, as further described below, in alternative implant embodiments the interior eyelets (126) can be used for securing the implant in place (e.g., can be used as internal retention eyelets located within the perimeter of the plate). Each interior eyelet (126) is connected to the first outer rim (124A) by an outer wire strut (127) and to the inner rim (122) by an inner wire strut (129). The interior eyelets (126) are connected to one another by a connecting wire strut (128) that extends between the eyelets (126). Inner, outer and connecting wire struts (127, 128, 129) are also coplanar with the inner rim (122) and first outer rim (124A).

Figure 15:
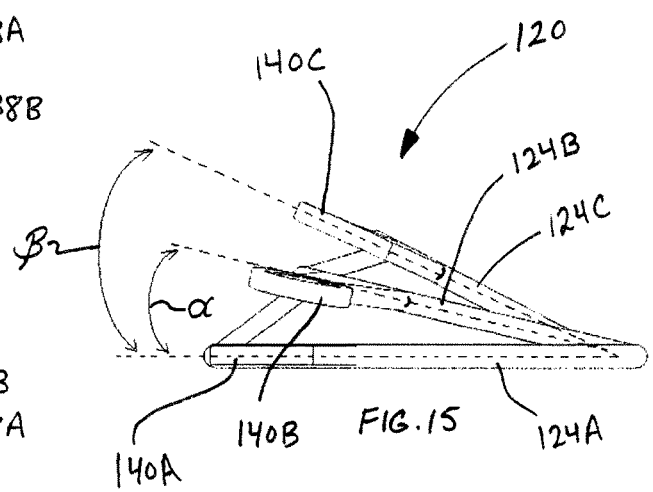

Support frame (120A) further includes second and third outer wire rims (124B, 124C), as shown. Second and third outer rims (124B, 124C) are curved similar to first outer rim (124A), but have progressively smaller radii of curvature. Second and third outer rims (124B, 124C) also are joined to inner rim (122) between outer corners (125), with third outer rim (124C) joined to inner rim (122) inwardly of second outer rim (124B) (as best seen in FIG. 6). Each of the outer wire rims (124A, 124B, 124C) thus comprises an arc that subtends an angle of between about 160 and about 240 degrees. While first outer rim (124A) is generally coplanar with inner rim (122), second and third outer rims (124B, 124C) extend away from the inner rim (122) at an angle thereto. As shown in FIG. 15, second outer rim (124B) extends away from the inner rim (122) at an angle (a) of between about 10 and about 20 degrees, while third outer rim (124C) extends away from the inner rim (122) at an angle (B) of between about 20 and about 30 degrees. Thus, the outer rims (124A, 124B, 124C) have a tiered arrangement, with the second and third outer rims (124B, 124C) extending upwardly away from the first outer rim (124A) at increasing angles thereto.

Second outer wire rim (124B) is further connected to and supported from the inner rim (122) by a pair of support struts (131) extending inwardly from the second outer rim (124B) to the inner rim immediately adjacent where third outer rim (124C) meets the inner rim (122), as shown. Similarly, the third outer wire rim (124C) is further connected to and supported from the inner wire rim (122) by a pair of support struts (132) extending inwardly from the third outer rim (124C) to the inner rim (122). In addition, wire support braces are provided between adjacent outer rims (124A, 124B, 124C). Thus, a first support brace (134) extends between the first and second outer rims (124A, 124B), and a second support brace (135) extends between the second and third outer rims (124B, 124C). The first support brace (134) intersects the first outer rim (124A) at approximately the midpoint of the first outer rim, and, when viewed from the top (FIG. 6), extends to the second outer rim (124B) at an included angle (γ) of less than 90 degrees (e.g., >45 up to about 60 degrees). Similarly, the second support brace (135) intersects the second outer rim (124B) at approximately the midpoint of the second outer rim, and, when viewed from the top (FIG. 6), extends to the third outer rim (124C) at an included angle of less than 90 degrees (e.g., >45 up to about 60 degrees).

Support struts (131, 132) and support braces (134, 135) are used to facilitate the manufacture of the standardized support frame, particularly when using additive fabrication methods such as selective laser melting ("SLM") or sintering ("SLS"). In addition, while complex designs fabricated using SLM or SLS often require complicated support structures, the support frame (120) can be designed to be self-supporting (or partially self-supporting) during SLM or SLS fabrication. This self-supporting aspect of the support frame mesh is provided by designing the support frame so that the wire segments of the mesh are angled with respect to the build plate by more than 45 degrees. The self-supporting nature of the support frame means that a support structure for the mesh as it is "printed" on an SLM build plate is not required during SLM, or may be required for only a portion of the support frame.

Since support struts (131, 132) and support braces (134, 135) are used primarily to facilitate the manufacture of the standardized support frame, they will often be removed during customization of the support frame for a particular patient in order to allow the rims (122, 124A, 124B, 124C) to be adjusted (or even removed entirely) as needed. However, in other instances (e.g., support frame (120A)), one or more of the support struts (131, 132) and support braces (134, 135) can remain in place.

Wire mesh support frame (120A) shown in FIGS. 6 and 7 is formed from a standardized support frame (120) described further herein. In the standardized support frame (120), the retention eyelets are connected to the first outer rim (124A) by a pair of retention arms (138A). However, in generating the modified support frame (120A) for the customized implant (110), one of the retention arms (138A) for each of the eyelets (140A) has been removed (by cutting using, for example, wire cutters). Similarly, each of the second and third outer rims (124B, 124C) on the standardized support frame (120) includes a pair of retention eyelets, each of which is connected to the rim by a pair of retention arms. In generating the modified support frame (120A) for the customized implant (110), these eyelets and retention arms associated with the second and third outer rims (124B, 124C) have been removed.

Figure 10:
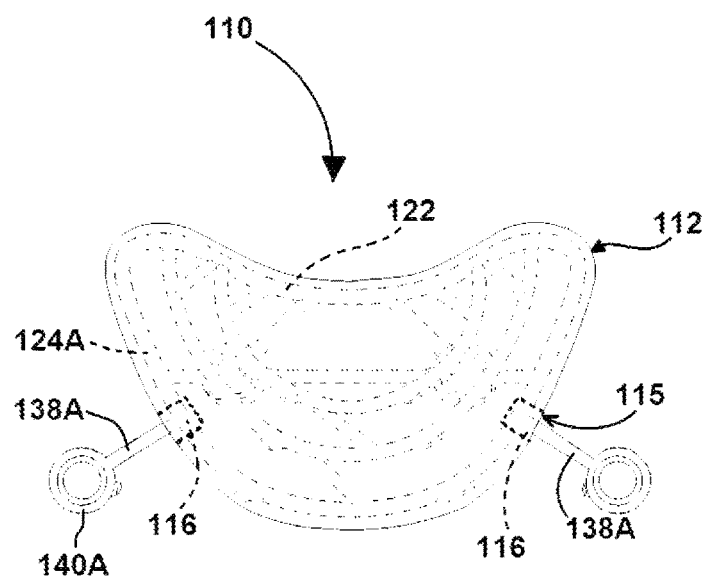
FIG. 10 is a top plan view of the paranasal implant of FIGS. 2-5, showing in hidden line the internal portions of the support frame and the open cavities in the biocompatible plate from which the retention arms extend out of the plate.

As mentioned previously, the retention arms (138A) extend out of the plate (112) through an aperture (115) that is larger in diameter than that of the retention arms (138A), and an open internal cavity (116) is provided in the plate material adjacent each aperture (115). The aperture (115) and associated cavity (116) are sized and configured such that the retention arms (138A) as well as a portion of the outer rim (124A) adjacent the retention arms (138A) is not covered by the plate material. Thus, the diameters of aperture (115) and the associated cavity (116) are larger than the outer diameter of the retention arm (138A) extending therethrough. In addition, as best seen in FIG. 10 wherein a cavity (116) and the portion of the retention arm (138A) and outer rim (124A) located within that cavity are shown in hidden line, the depth of each cavity (116) is greater than the length of the portion of the retention arm located within the cavity. In this manner, no portion of the retention arm (138A) is in contact with the cement of the plate (112) and at least a portion of the outer rim (124A) adjacent the interior end of the retention arm is also located within the cavity (116) (i.e., is not covered by cement). As mentioned previously, this allows the retention arms (138A) to be bent considerably without risk of cracking the plate material.

Figure 8:
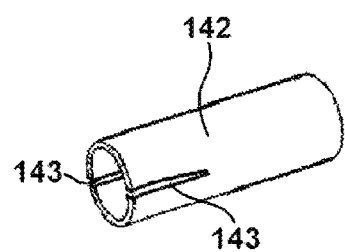
FIG. 8 depicts a guard member used when molding a biocompatible plate around a support frame such as that used in the paranasal implant of FIGS. 2-5.
Figure 9:
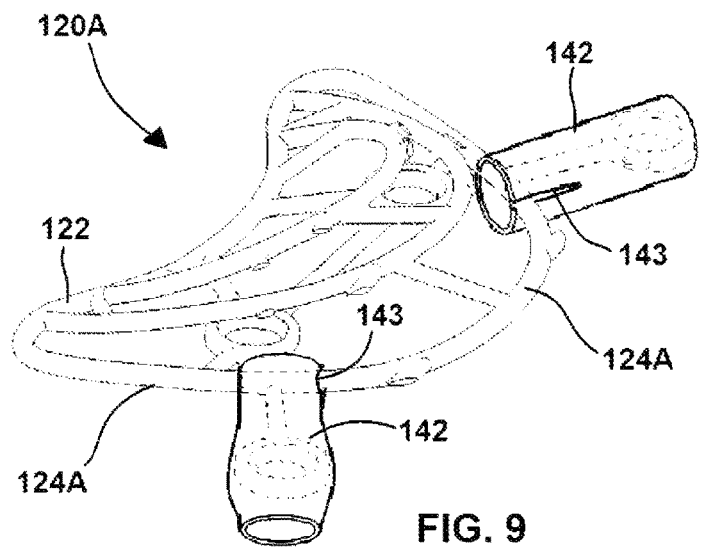
FIG. 9 depicts the positioning of the guard member of FIG. 8 on the support frame prior to molding of the biocompatible plate over the support frame.
Figure 10A:
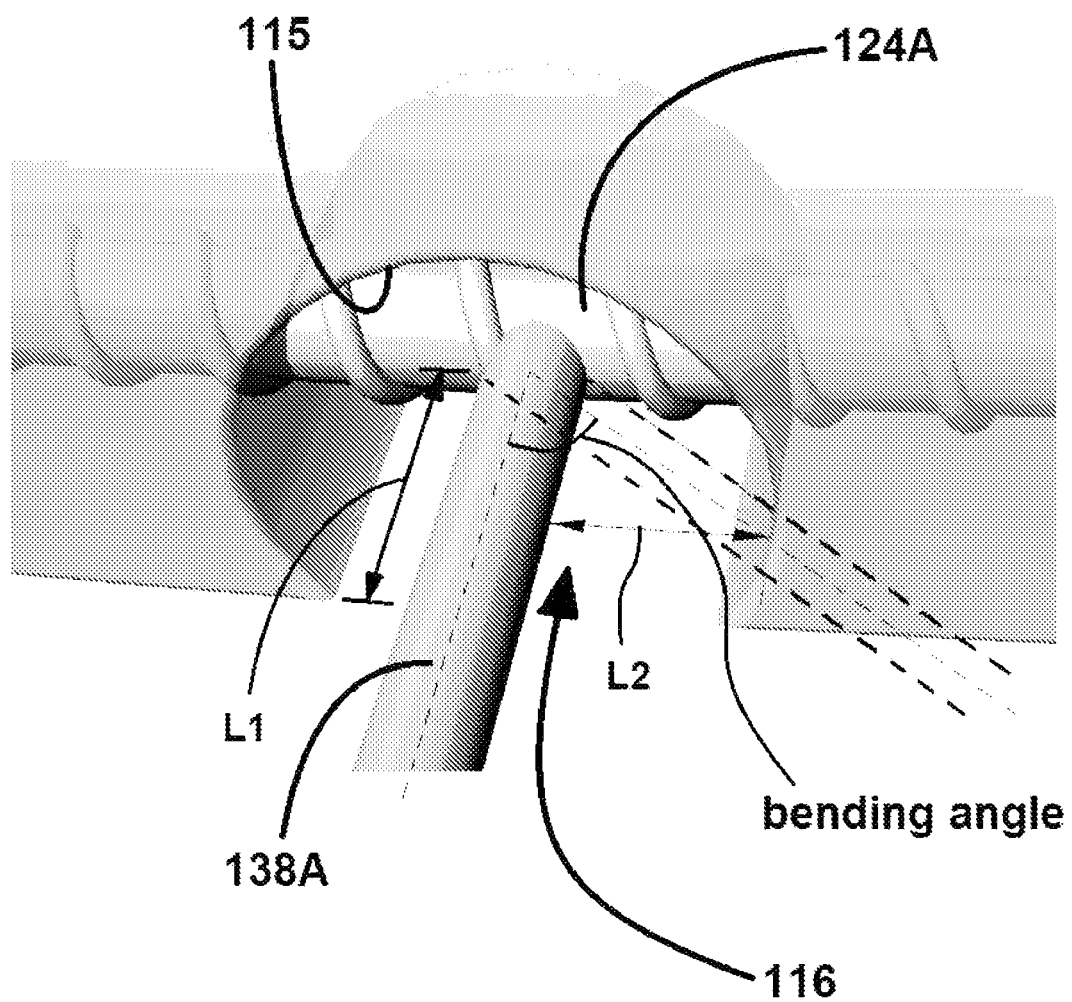
FIG. 10A is an enlarged view of a portion of the implant of FIGS. 2-5, depicting the open cavity and the portion of the retention arm and outer rim located therein.
Figure 11:
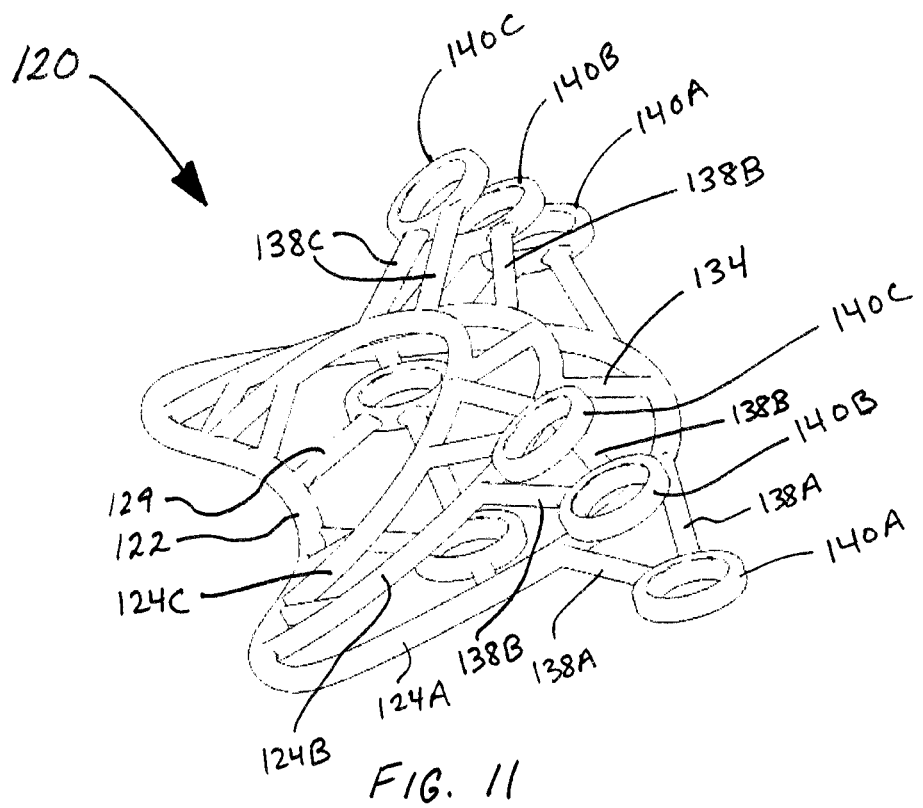
FIG. 11 is a view similar to that of FIG. 7, depicting a support frame in its standard, unmodified form.
Figure 12:
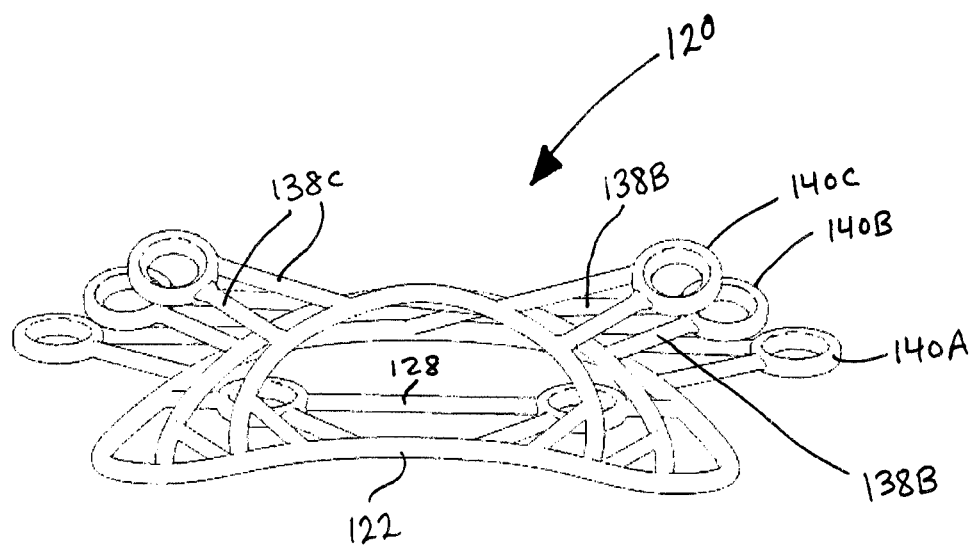
FIGS. 12-16 are front elevational, top plan, bottom plan, side elevational, and front views, respectively, of the unmodified support frame of FIG. 11.

FIGS. 8-10 depict one manner of forming the apertures (115) and cavities (116) during the molding of the cement plate. A guard is positioned over each of the retention arms (138A) and a portion of the outer rim (124A) where the retention arms (138A) are joined thereto. The guards may optionally also cover the retention eyelets (140A), although this is not necessary when the retention eyelets (140A) are located outside of the mold cavity for the plate. The guards act as barriers between the cement and the retention arms and a portion of the outer rim during the molding process, thus preventing the cement from hardening over the retention arms and protected portion of the outer rim.

In the embodiment shown in FIGS. 8 and 9, each guard comprises a silicone sleeve (142) having a pair of slits (143) located on opposite sides of the sleeve and extending from one and of the sleeve (142) along a portion of its length. As shown in FIG. 9, after the support frame (120A) has been formed into the desired shape (e.g., by cutting off unneeded eyelets, retention arms, etc.), a sleeve (142) is slid over each of the remaining retention arms (138A) and associated eyelets (140A). The slits (143) allow the sleeve (142) to also be slid over the portion of the outer rim (124A) adjacent the retention arms (138A), as shown. One the sleeves (142) are in place, the support frame (120A) is placed into a mold for the plate (112). After the molding process is complete, the sleeves (142) are removed, with each sleeve leaving behind a cement-free cavity (116) and aperture (115) through which a retention arm (138A) extends, as shown in FIGS. 10 and 10A. At the time of implantation, the surgeon can then deform the retention arms (138A) as necessary for proper fit and placement, without cracking the cement plate (112). It will be understood that the size of the apertures and cavities can be modified depending on the amount of retention arm deformation that is anticipated to be required at the time of implantation.

Turning now to the standardized, unmodified wire mesh support frame (120), FIGS. 11-16 depict the various aspects and features thereof. First, it should be pointed out that the only difference between the modified support frame (120A) described above and support frame (120) is that, in the modified version, the retention arms (138B, 138C) and eyelets (140B, 140C) associated with the second and third outer wire rims (124B, 124C), as well as one of each pair of retention arms (138A), had been removed. These features are present in the standardized, unmodified wire mesh support frame (120) shown in FIGS. 11-16.

Figure 13:
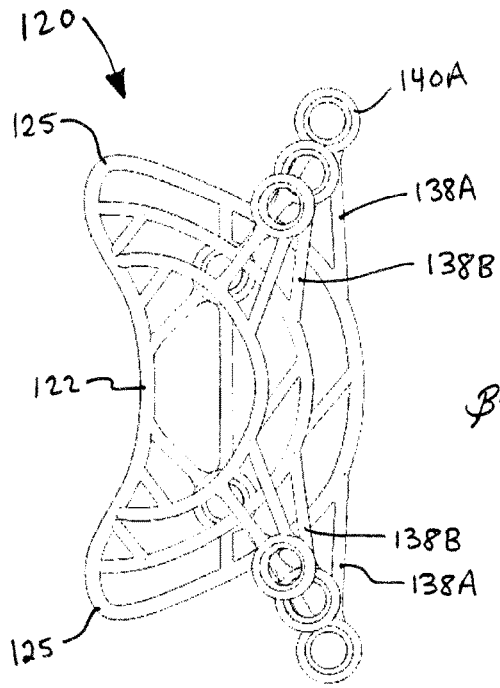
Figure 16:
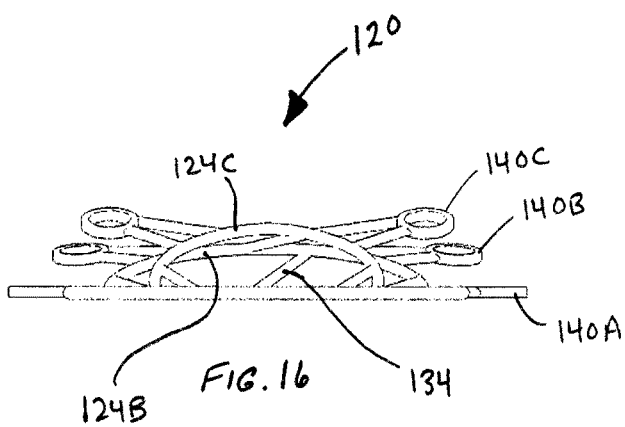

Thus, each of the outer wire rims (124A, 124B, 124C) includes a pair of retention eyelets (140A, 140B, 140C), each of which is supported by a pair of retention arms (138A, 138B, 138C), as shown. The retention eyelets (140A, 140B, 140C) are generally located along opposite sides of their respective outer rims (124A, 124B, 124C). Since the second and third outer rims (124B, 124C) are angularly tiered with respect to the first outer rim (124A), the second and third pairs of retention eyelets (140B, 140C) are located at successively higher elevations with respect to the first pair of retention eyelets (140A), as best seen in FIGS. 15 and 16. Similarly, the second and third pairs of retention eyelets (140B, 140C) are located at successively shorter distances from the inner rim (122), as best seen in FIGS. 13 and 14.

Figure 14:
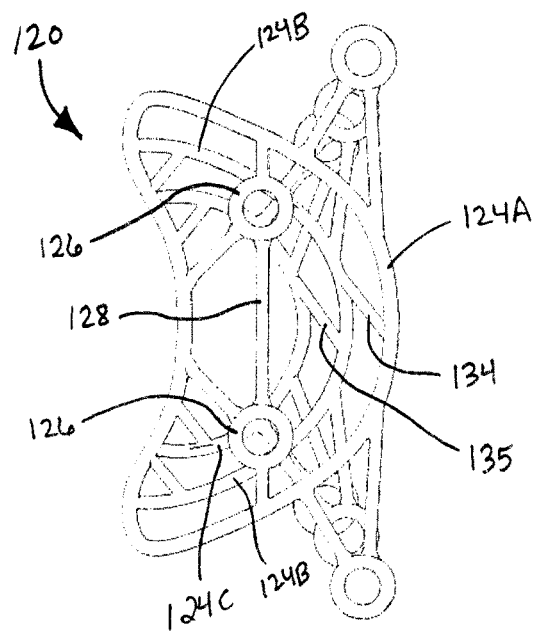

As best seen in the bottom plan view of FIG. 14, interior retention eyelets (126) are located approximately between the second and third wire outer rims (124B, 124C). This arrangement allows the interior eyelets (126) to be employed in some implants for internal fastening without removing the second and third wire outer rims (124B, 124C) (although one or both rims may need to be bent in order to do so). In addition, this allows for the fabrication of smaller implants that utilize the retention eyelets (140C) associated with the third outer rim (134C), with the interior eyelets located within the molded plate for added strength and rigidity.

While the various wire features and eyelets can have a variety of sizes and configurations, in the embodiment shown the wire rims (122, 124A, 124B, 124C), wire support struts (127, 128, 129, 131, 132) and wire support braces (134, 135) have a circular cross-section and a diameter of between about 0.5 and about 1.2 mm. It will be understood, however, that the various wire features can have other cross-sectional shapes (e.g., to increase rigidity and/or strength) and can have varying thicknesses. As seen in FIGS. 11-16, the eyelets (140A, 140B, 140C, 126) have a thickness similar to that of the wire members (e.g., between about 0.4 and about 0.7 mm).

Given their thickness and material (e.g., titanium), the various wire features are not only deformable but also are easily cut using, for example, conventional wire cutters. This allows the standardized support frame (120) to be readily modified and manipulated to suit a variety of implant shapes and sizes, as well as to accommodate a wide variety of fastening locations (e.g., to position the fastening points where there is sufficient underlying bone to accept a bone screw).

Figure 17A:
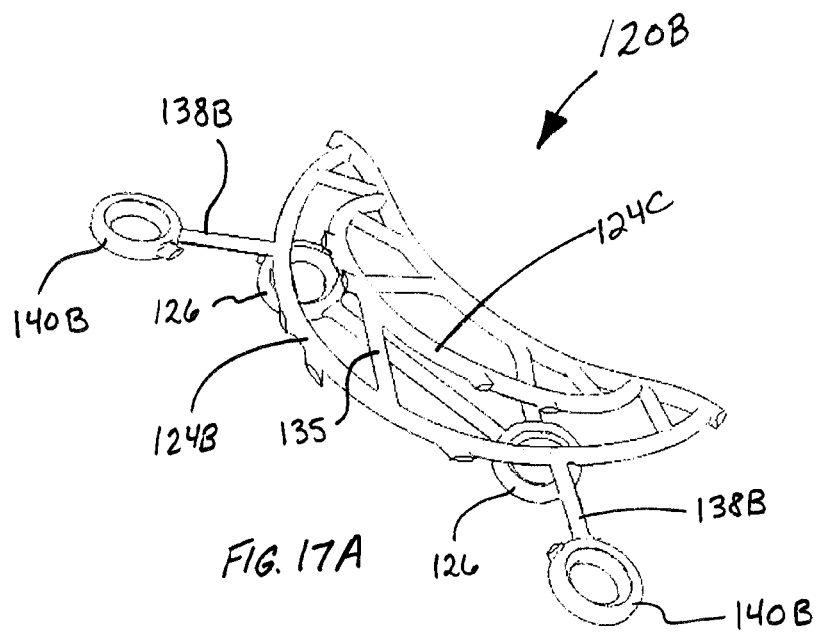
FIG. 17A is an orthogonal view of an alternative embodiment of a support frame, fabricated from the unmodified support frame of FIG. 11.
Figure 17B:
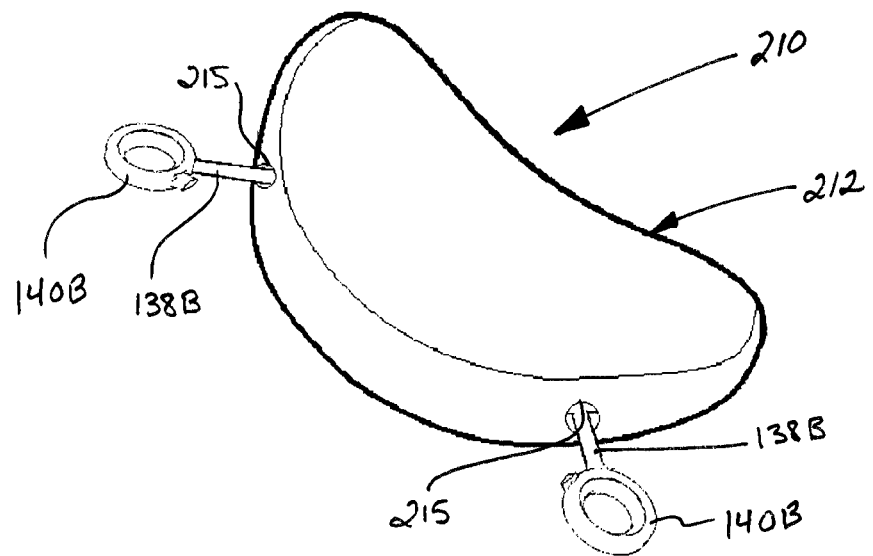
FIG. 17B depicts an alternative paranasal implant fabricated using the support frame of FIG. 17A.

For example, when a smaller implant (in terms of perimeter and/or thickness) is desired, the first outer rim (124A) can be removed entirely, along with the eyelets (140C) and retention arms (138C) associated with the third outer rim (124C) and one of the retention arms (138B) of each pair supporting a retention eyelet (140B), as shown in FIG. 17A. In this manner, a modified support frame (120B) is produced, and is used to internally support the molded plate (212) of the paranasal implant (210) shown in FIG. 17B. As also seen in FIG. 17A, the interior eyelets (126) remain on the support frame (120B), however, the outer wire support struts (127) have been removed. Depending on the desired thickness of the cement plate (212) of the implant (210), the angle between the second and third outer rims (124B, 124C) (i.e., B minus a in FIG. 15) can be decreased simply by compressing the modified support frame (120B). If necessary, second support brace (135) can be removed in order to allow for further compression of the support frame (120B) to accommodate an even thinner plate (212) while still providing the support and strength of both the second and third outer rims (124B, 124C).

Once the modified support frame (120B) has been formed, the silicone sleeves (142) described previously are placed over the two remaining retention arms (138B) and adjacent portions of the second outer rim (124B). The support frame (120B) is then inserted into the customized mold for the plate (212) and the cement precursor mixture injected into the mold having the support frame positioned therein. Following hardening and removal of the silicone sleeves, the implant (210) is provided, with the retention arms (138B) extending out of the cement plate (212) through enlarged apertures (215). The implant (210) is then implanted into the patient, with the retention arms (138B) deformed at the time of implantation to ensure proper positioning of the retention eyelets (140B), as described previously.

Figure 18A:
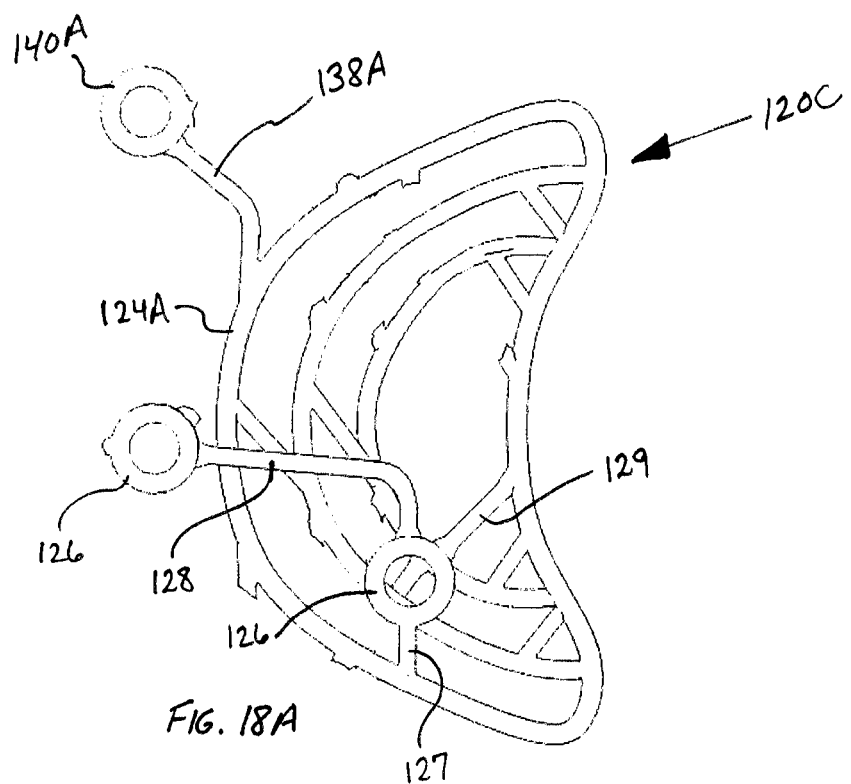
FIG. 18A is a top plan view of another alternative embodiment of a support frame, fabricated from the unmodified support frame of FIG. 11.
Figure 18B:
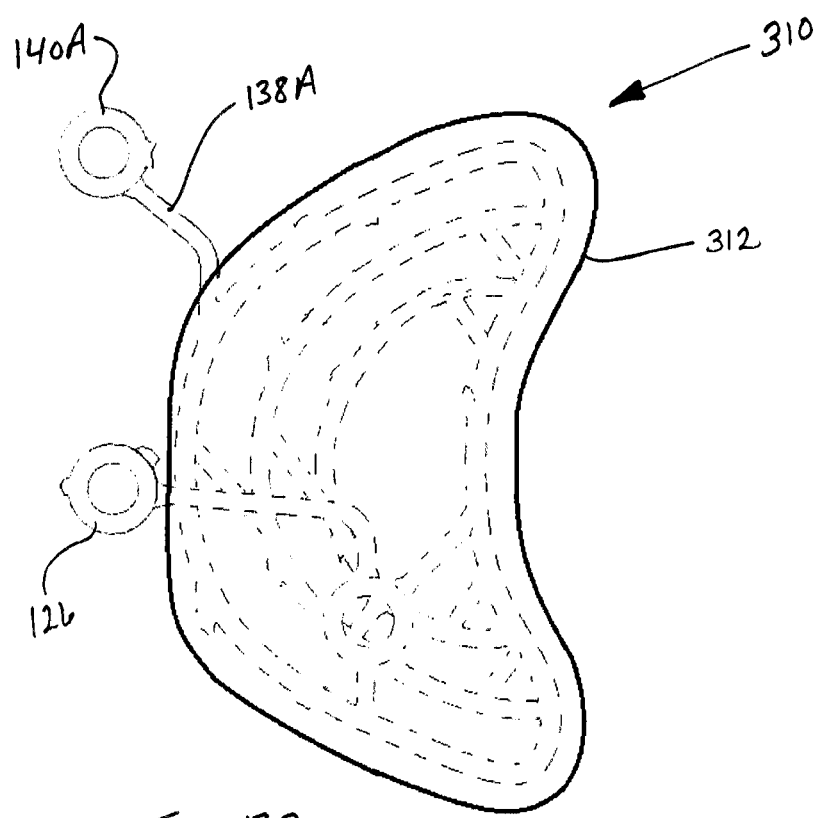
FIG. 18B is a top plan view of an alternative paranasal implant fabricated using the support frame of FIG. 18A.

FIGS. 18A and 18B depict yet another modified support frame (120C) used to fabricate an implant (310) having a customized cement plate (312). In this instance, although the implant (310) once again has a pair of retention eyelets for securing the implant in a patient, one of these is an interior eyelet (126) that has been relocated outside the perimeter of the outermost rim (124A). The other interior eyelet (126) remains within the perimeter of the modified support frame (120C), and hence within the plate (312) following molding, thereby providing additional strength and support to the implant.

In order to move one of the interior eyelets (126) outside the perimeter of the support frame (120C), and hence the cement plate (312), the inner and outer struts (127, 129) attaching that interior eyelet (126) to the rims (124A, 122) are removed. Thereafter, connecting strut (128) is bent as shown in order to move the partially detached interior eyelet (126) outside of the first outer rim (124A). In this manner a retention eyelet, namely, the relocated interior eyelet (126), can be positioned at a location that one of the other retention eyelets is unable to be relocated to without positioning its retention arm outside of the perimeter of the cement plate (312). It will be understood that any of the retention eyelets (140A, 140B, 140C, 126) can be repositioned by removing one or more of its supporting wire members (e.g., retention arms (138A, 138B, 138C) and struts (127, 128, 129)) and bending the remaining support wire member to position the eyelet at the desired location. In addition, more than two retention eyelets may be so positioned in order to provide more than two fastening points.

In addition to bending or removing the various supporting wire members (138A, 138B, 138C, 127, 128, 129) for the various eyelets (140A, 140B, 140C, 126), portions of the inner rim (122) and the outer rims (124A, 124B, 124C) also can be removed and/or deformed (e.g., twisted or otherwise bent) in order to modify the support frame (120) to the desired shape. In general, the outer perimeter of the support frame is manipulated so as to generally correspond to the outer shape of the cement plate. In most instances, the outer perimeter of the modified support frame will be slightly smaller than the cement plate so that, following molding of the plate, only the retention eyelet(s) to be used for fastening the implant in place and their respective supporting wire member will be located outside of the molded plate.

Figure 19:
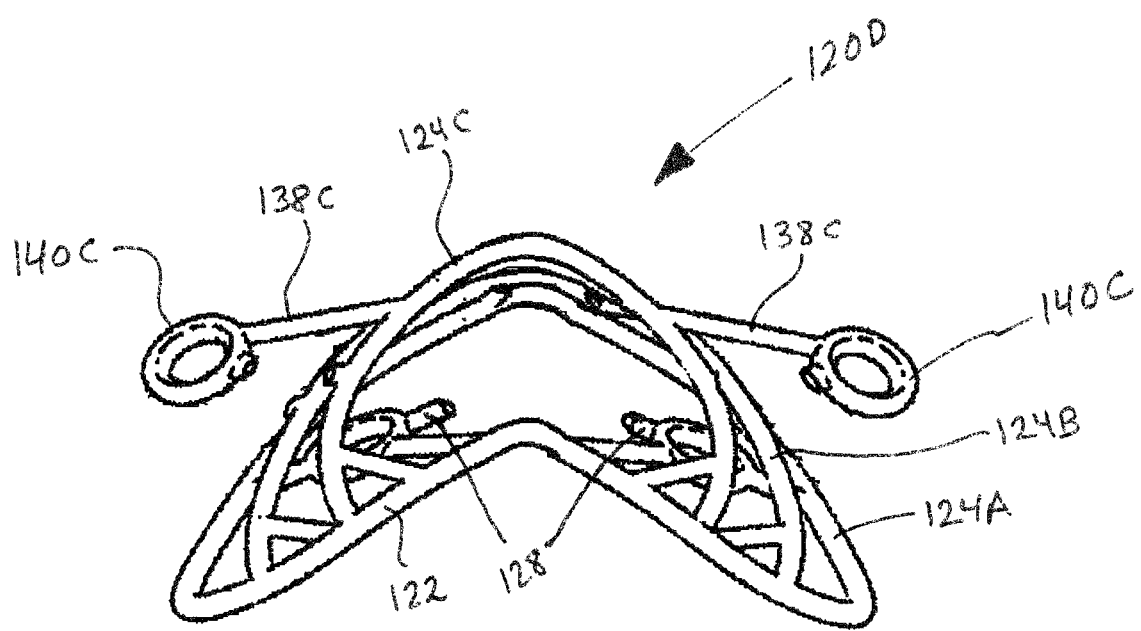
FIG. 19 is a front elevational view of yet another embodiment of a support frame, fabricated from the unmodified support frame of FIG. 11, for use in fabricating a paranasal implant.

By way of example, FIG. 19 depicts yet another modified support frame (120D) fabricated using the standardized support frame (120). In this embodiment, retention eyelets (140A, 140B) and their associated retention arms (138A, 138B) also have been removed, along with one of the retention arms (138C) for each retention eyelet (140C) associated with the third outer rim (124C). In addition, the majority of connecting strut (128) has been removed (i.e., cut out), along with first and second support braces (134, 135), thus allowing the support frame (120D) to be bent as shown.

Figure 20A:
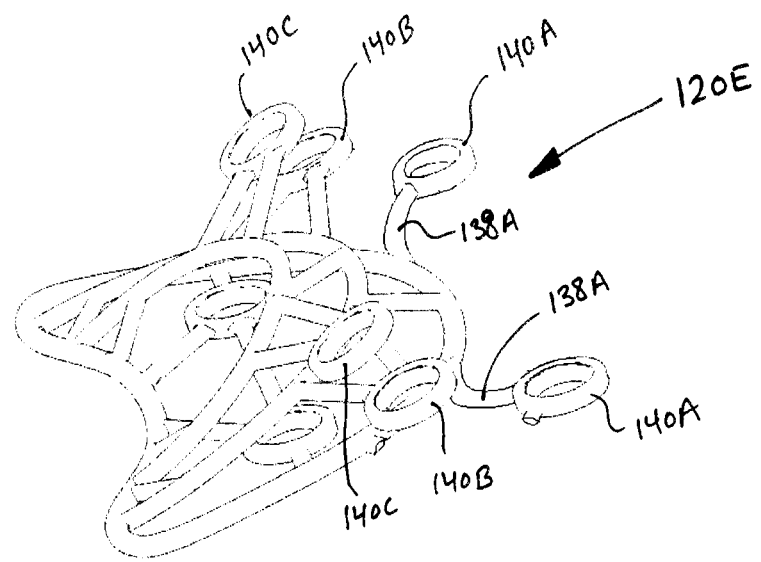
FIG. 20A is an orthogonal view of another alternative embodiment of a support frame, fabricated from the unmodified support frame of FIG. 11.
Figure 20B:
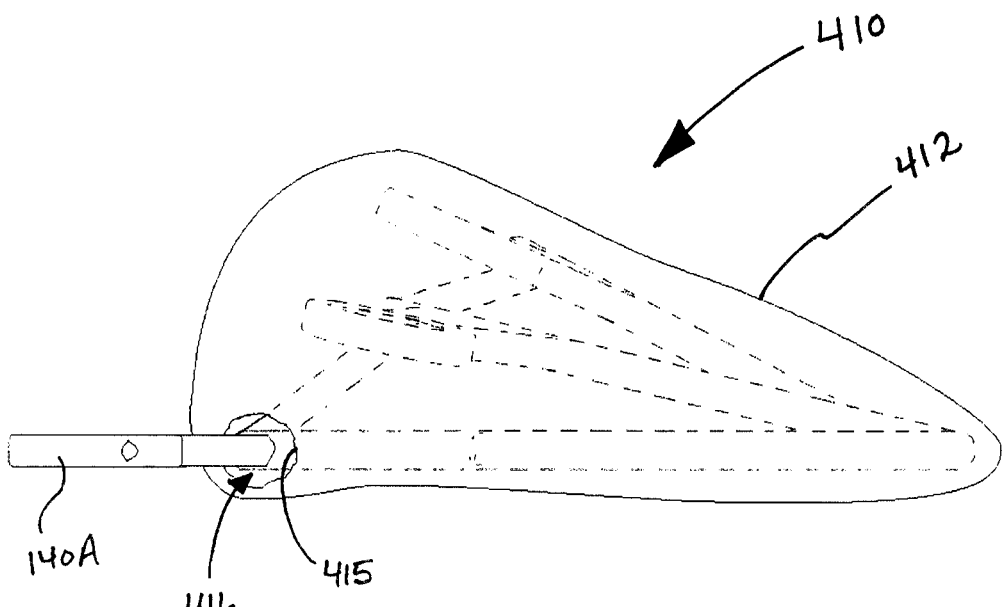
FIG. 20B is a side view of an alternative paranasal implant fabricated using the support frame of FIG. 20A.
Figure 21A:
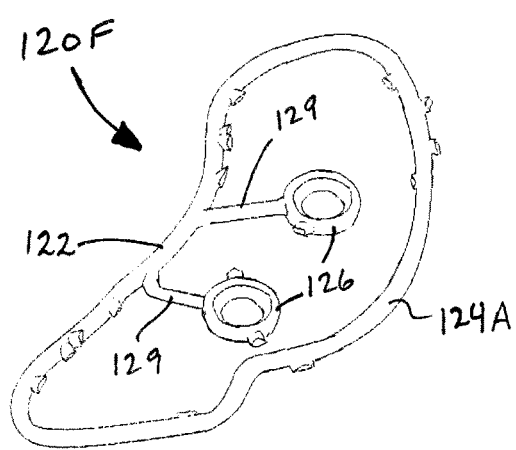
FIG. 21A is an orthogonal view of yet another alternative embodiment of a support frame, fabricated from the unmodified support frame of FIG. 11, for use in the alternative paranasal implant shown in FIGS. 21B, 22 and 23.
Figure 21B:
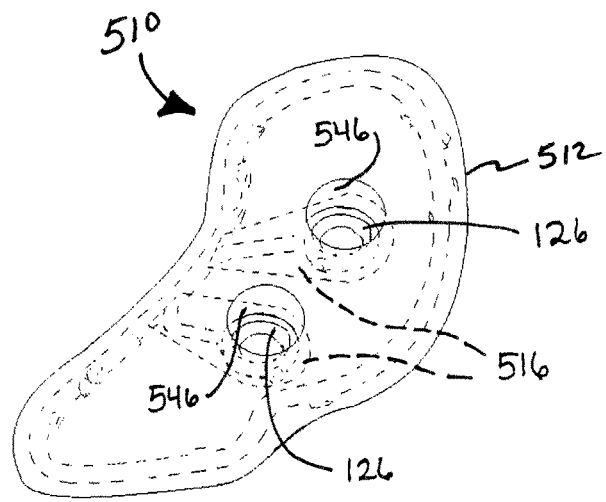
FIGS. 21B and 22 are orthogonal views of the upper surface of the implant.
Figure 22:
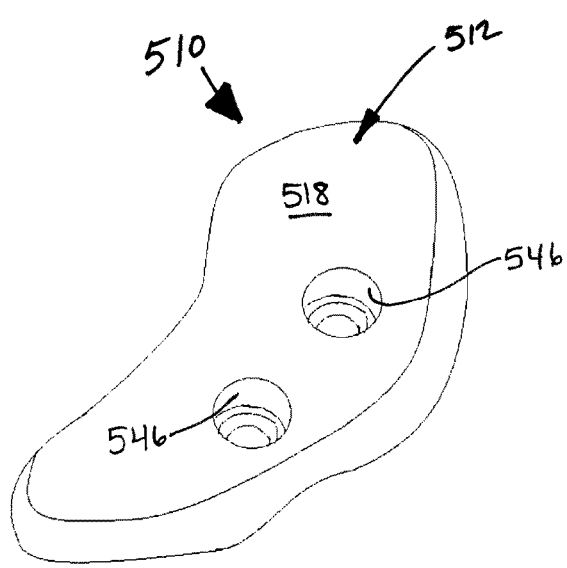

While unused retention eyelets (140A, 140B, 140C) and other portions of the support frame (120) that would otherwise be located outside of the cement plate are typically removed, in some instances retention eyelets not used for securing the implant in a patient remain inside of the cement plate. For example, in the embodiment shown in FIGS. 20A and 20B, the customized cement plate (412) has sufficient thickness and width to allow the retention eyelets (140B, 140C) associated within the second and third outer wire rims (124B, 124C) to be located within the plate (412) of the implant (410). One of the retention arms (138A) for each of the external retention eyelets (140A) has been removed, as shown, and the remaining retention arm (138A) then bent so as to locate the attached eyelet (140A) outside of the cement plate following molding. As in the previous embodiments, the plate (412) is molded about the support frame (120E) such that the retention arms (138A) and a portion of the first outer rim (124A) adjacent the retention arms (138A) is not covered by the plate material (e.g., cement). Thus, not only does each of the retention arms (138A) extend out of the plate (412) through an aperture (415) that is larger in diameter than that of the retention arms (138A), an internal cavity (416) is also provided in the plate material adjacent each aperture (415). By providing such internal cavities (416) and oversized apertures (415), retention arms (138A) can be bent considerably without risk of cracking the plate material.

As mentioned previously, eyelets located within the perimeter of the plate can be used for securing the implant in place instead of (or in addition to) eyelets located outside of the perimeter of the plate (e.g., as in the embodiments of FIGS. 2-20B). Eyelets "located within the perimeter of the plate" simply means that the eyelets are not located in spaced apart relationship to the plate. Instead, although such eyelets are not encased in the plate material, they are located within cavities formed in the plate material. One such embodiment is shown in FIGS. 21A-23, wherein the standardized support frame (120) has been modified to allow for the use of the interior eyelets (126) for fastening the implant (510) in place in a patient. In this instance, retention eyelets (140A, 140B, 140C) and other portions of the support frame (120F) that would otherwise be located outside of the plate (512) have been removed. In particular, the second and third outer wire rims (124B, 124C) have been removed entirely, as well as outer struts (127) and connecting strut (127), leaving only inner rim (122), first outer rim (124A), interior eyelets (126) and inner struts (129), which serve as retention arms that connect the interior eyelets (126) to the inner rim (122). In addition, the inner and outer rims (122, 124A), as well as the inner struts (129) have been deformed (bent) so as to not only provide support frame (120F) with an outer perimeter shape generally corresponding to that of the plate (512) to be molded thereabout, but also to position interior eyelets (126) at the desired location. It will be understood, however, that, depending on, for example, the thickness and overall size of the plate, other portions of the support frame need not be removed in order to use the interior eyelets (126) for securing the implant in a patient.

Following modification and manipulation of the standardized support frame (120) to provide modified support frame (120F), the modified support frame (120F) is positioned within a mold for the plate (512). However, in order to employ the interior eyelets (126) for fastening purposes, the eyelets must be accessible to the surgeon, such as through the thickness of the plate. In addition, it is also desirable that, upon placement in a patient, the bottom surface of the interior eyelets (126) lie against the surface of the bone or other tissue into which the fasteners will be inserted for securing the implant in place.

As seen in FIGS. 21B-23, a cylindrical bore (546) extends through the thickness of the plate (512) between the upper (i.e., outer) and bottom (i.e., bone-facing) surfaces (518, 517) of the plate, directly above each of the interior eyelets (526). Fasteners such as bone screws are inserted through the bores (546) and through the eyelets (526) into bone or other tissue at the implantation site. In the embodiment shown, the diameter of each bore (546) is slightly larger than the interior diameter of the eyelets (526) in order to not only facilitate insertion of a bone screw or other fastener through the bore, but also to prevent damage to the cement plate during implant securement. As will be described in more detail with respect to the fabrication of supraorbital implant (710), bores (546) are formed during molding, such as by positioning a cylindrical member (e.g., a silicone rod) within the mold directly above eyelets (126) so as to prevent the cement from forming and hardening over the eyelets. Following cement hardening, the cylindrical members are removed, leaving bores (546) in the cement directly above the eyelets (126).

Despite the precision by which the customized plate (512) can be fabricated and the support frame (120F) manipulated to the proper shape prior to molding, the position of eyelets (126) will often need to be adjusted, particularly at the time of implantation. In addition, implant securement in a patient typically causes some movement of the eyelets (126) as a result of, for example, imprecise drilling of pilot holes in the bone for receiving the bone screws (or other fasteners) or the off-axis threading of a bone screw (e.g., when self-tapping screws are used, in which case no pilot holes are necessary). While the insertion of the first bone screw through one of the eyelets (126) will cause little or no movement of the eyelet, the insertion of a bone screw through the second eyelet (126) will often cause movement of that eyelet (126).

Figure 23:
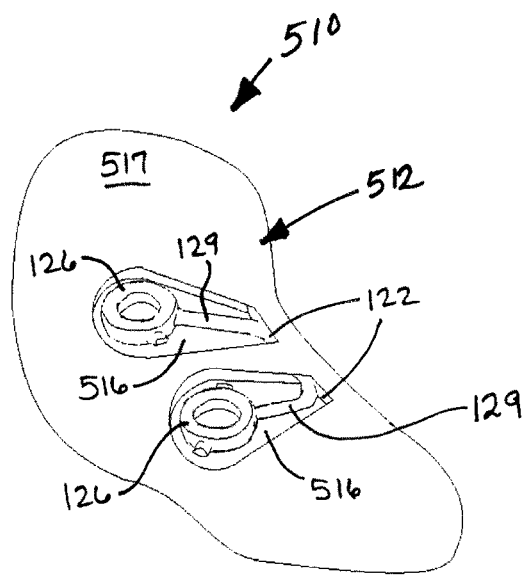
FIG. 23 is a bottom view of the implant.
Figure 24:
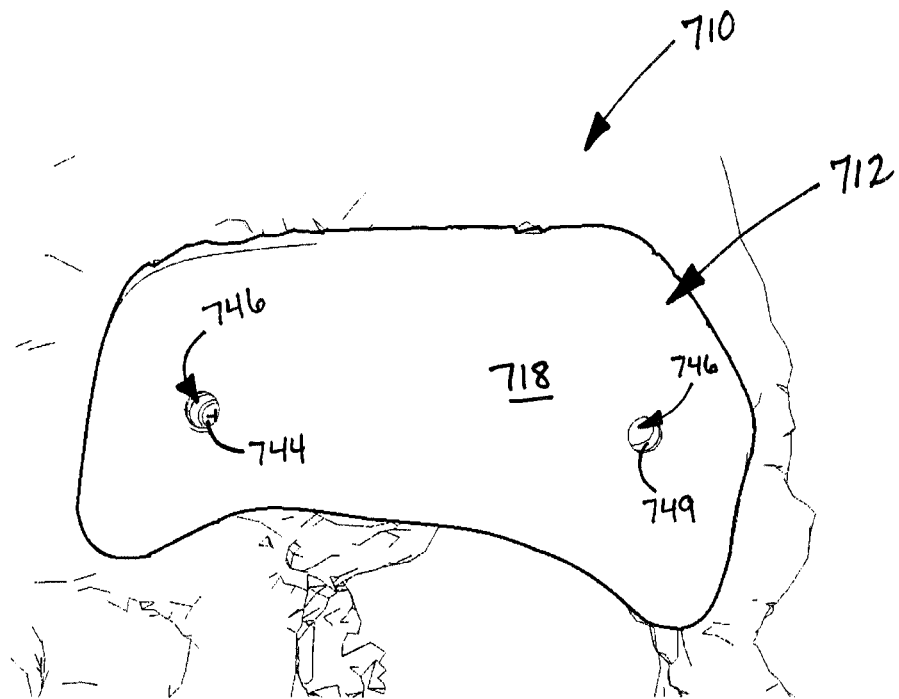
FIG. 24 is an enlarged view of a portion of FIG. 1, showing the supraorbital implant in greater detail.
Figure 25:
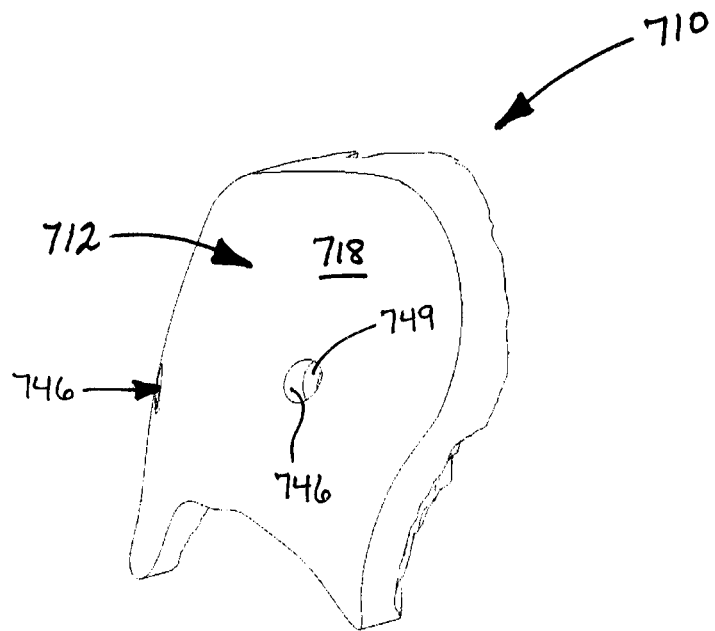
FIGS. 25-27 are side, bottom and angled bottom views, respectively, of the implant of FIG. 24.

In order to not only allow for adjustment of the eyelets (126) at the time of implantation but also to allow for movement of the eyelets during fastening without risk of cracking the plate (512), the plate is molded such that open cavities (516) are provided in the bottom, bone-facing surface (517) of the implant (see FIG. 23). These cavities (516) are sized, shaped and located such that the eyelets (126), wire support struts (129) (which serve as retention arms for the eyelets), and, optionally, a portion of the inner rim adjacent the struts (129), are not encased in the cement (or other plate material). In the particular embodiment shown, the eyelets (126) essentially float within the cavities (516), allowing the eyelets to move up and down and side-to-side within the cavities (516), either as a result of manipulation by the surgeon at the time of implantation or as a result of the fastening process during implantation. Thus, in the depicted embodiment, the cavities (516) are deeper than the thickness of the eyelets (126) and support struts (129), and are sized to provide space between the eyelets (126) and the sidewalls of the cavities. For example, the spacing between an eyelet (126) and the sidewalls of the cavity (516) is about 0.5 to about 3 mm, or about 1 to about 2 mm. The spacing between an eyelet (126) and the bottom surface of the cavity (516) is about 0.25 to about 3 mm, or about 0.5 to about 1.5 mm. Similar spacings can be employed for the cavities on implant (710) and the mandibular implants, as well as any other implants in accordance with the present disclosure that employ internal retention eyelets.

The cavities (516) can be formed in a variety of manners, such as by positioning a suitably shaped guard over the eyelets (126) and support struts (129) (and optionally a portion of inner rim (122)). The guard can be configured similar to sleeve (142) described previously. Alternatively, the guard can comprise a cover similar to that described further herein in connection with the supraorbital implant.

While a number of different modified support frames (120A-F) have been shown and described, it will be understood that an endless number of alternative modified support frames can be made starting from standardized support frame (120). Any number of the eyelets (140A, 140B, 140C, 126) can be used for securing the implant in place. While these eyelets are attached to the unmodified support frame (120) by at least two wire members (e.g., retention arms (138A, 138B, 138C), in some embodiments of the final modified support frame the eyelets used for fastening purposes are only attached to the support frame by a single wire member in order to facilitate manipulation of the positioning of the eyelet both at the time of fabrication and at the time of implantation. The use of at least two wire members for attaching each eyelet to the support frame at the time the standardized support frame (120) is fabricated (e.g., via selective laser melting) not only provides a more rigid support frame that is easier to manufacture, but also increases the range of placement options of each eyelet during subsequent modification of the support frame (120). Of course in other embodiments one or more of the eyelets remaining on the modified support frame can remain attached to the support frame by both of the original retention arms.

Various components of the support frame (120) can be removed or deformed in order to alter the shape of the support frame as needed for a particular implant. For example, one or both of the first and second support braces (134, 135) can be cut off to allow for greater bending of the support frame, such as to increase or decrease the height of the support frame by bending the outer rims (124A, 124B, 124C) away from or towards each other.

While the support frame (120) has been described in connection with the fabrication of a customized paranasal implant, this same support frame can be used in fabricating various other bone implants, particularly those for craniofacial use. For example, the paranasal implants described above can be used, with or without further modification, for such as the zygoma, supraorbital or maxilla reconstruction.

Turning to the supraorbital implant (710) depicted in FIG. 1 as well as FIGS. 24-29, this implant (710) is similar to the paranasal implant in that it includes a biocompatible plate (712) and an internal wire mesh support frame (720A) (see FIG. 29) having a pair of fastening points. Like paranasal implant (510), the fastening points on supraorbital implant (710) comprise two eyelets (726) located within the bounds of the outer perimeter of the plate (see FIG. 26). The retention eyelets (726) are located within cavities (716) provided in the bottom (bone-facing) surface (717) of the plate (712), at the base of bores (746) that extend through the thickness of the plate (712) between the upper (i.e., outer) and bottom (bone-facing) surfaces (718, 717) of the plate. Each eyelet is connected to the internal portion of the support frame (720A) by a retention arm comprising a single wire strut (727) attached to the rim (722) of the support frame.

Each of the eyelets (726), the wire struts (727) and portions of the rim (722) adjacent the wire struts (727) are free of cement, such that the eyelets (726) and struts (727) float within their respective cavities (716). Thus, the cavities (716) are deeper than the thickness of the eyelets (726) and the diameter of the struts (727) such that each eyelet (726) and strut (727) is spaced away from the bottom surface (719) of their respective cavities (716). The bottom face, i.e., the bone-facing surface (726A) of each eyelet is approximately flush with the bottom surface (717) of the plate prior to implantation. In alternative embodiments, the upper face of one or both eyelets is located on the bottom surface (719) of its cavity (716) but is still free to slide across that bottom surface (719) so as to allow movement of the eyelet without risk of cracking the plate material. In addition, in alternative embodiments the bottom face, i.e., the bone-facing surface (726A) of each eyelet extends beyond the bottom surface (717) of the plate prior to implantation (i.e., is not flush therewith), or is located below the level of the bottom surface (717) of the plate (i.e., the cavities are deeper than those depicted in the figures).

Due to the thickness of the plate (712), bores (746) are longer in length than the bore (546) of paranasal implant (510). Because of this additional length, the bores (746) are more susceptible to being damaged during installation, particularly from a screwdriver or other implement inserted therethrough (e.g., a screwdriver used to drive a bone screw through an eyelet (726) into underlying bone). In order to help prevent such damage and to provide added strength and support to the implant (710), at least a portion of each bore (746) can be lined with a protective sleeve. In the depicted embodiment, an upper portion of each bore (746) includes cylindrical sleeve (749). Cylindrical sleeves (749) are formed integrally with the mesh support frame. During the plate molding process, at least the interior of the sleeves (749) is protected so that cement will not fill the sleeve. In fact, the same guard member (e.g., a silicone rod or similar member) used to protect the interior of the sleeves (749) from cement can also be used to form the bores (746), as further explained below. As a result, each cylindrical sleeve (749) is axially aligned with one of the eyelets (726), with a straight, cylindrical bore (746) extending therebetween. While the cylindrical sleeves (749) can be flush with the outer surface (718) of the plate (712), in the embodiment shown each sleeve (749) is spaced inwardly from the outer surface (718) of the plate.

Implant (710) is sized, shaped and configured to meet the specific needs of a specific patient. Thus, the shape and dimensions of plate (712) shown in the drawings is merely exemplary. In general, the outer surface (718) is smooth and curved to not only match surrounding bone and other tissue, but also to provide an aesthetically pleasing appearance. The goal of the supraorbital implant (710) is to mimic the appearance of a normal cranial shape in the region above an eye socket. The bottom, or bone-facing surface (717) is contoured to match the shape of the underlying bone and other tissue (where bone and other tissue is present), and, where bone is missing, avoid underlying tissue that will be protected by the plate (712) (e.g., brain tissue). In addition, the location of the eyelets (726), and hence the bores (746), is chosen to not only allow the implant (710) to be adequately secured in place, but also to ensure that there is sufficient underlying bone beneath the eyelets for receiving a bone screw or other fastener driven through the eyelet. In addition, the angle of the bore is also determined based on the planned surgical approach with respect to securing the implant in place, including optimizing the amount of bone available for securement as well as facilitating the surgical procedure itself.

During implantation, once the implant (710) is properly positioned in a patient, a bone screw (744) or other fastener is inserted into the plate through each of the bores (746), through the underlying eyelets (726) and into the underlying bone. As each bone screw (744) is threaded into the underlying bone, the eyelet (726) through which it extends will be pulled toward the bone until the bone-facing surface (726A) of the eyelet (726) is flush against the bone. The wire strut (727) to which the eyelet is attached will typically flex (i.e., deform) away from its cavity (716) to some extent, and perhaps laterally within the cavity as the bone screw is tightened. However, the cement of the plate (712) generally will not crack due to the fact that the cement does not cover the eyelet (726) or its supporting strut (727).

While two bone screws driven through the bores and eyelets into underlying bone will usually be sufficient to secure the implant (710) in place, it will be understood that more than two eyelets and associated bores may be provided on the implant (710)—particularly for larger implants and/or when there is some uncertainty ahead of time of the optimal fastening locations. For example, three (or more) retention eyelets (726) for receiving bone screws may be provided on the implant (710), but less than all of them (e.g., two) used for securing the implant in place. One or more externally located retention eyelets, each supported by one or more retention arms similar to implant (110), can also be provided in addition to the interior eyelets (726). Such external retention eyelets (i.e., located outside of the outer perimeter of the plate (712)), offer additional fastening locations for the surgeon when, for example, one or more of the interior eyelets cannot be used. These external retention eyelets are constructed similar to those provided on implant (110) described above, including the oversized apertures and cavities for preventing the cracking of the cement plate. In addition, one or more of such external retention eyelets and their associated retention arms can be removed by the surgeon at the time of implantation if it turns out that they are not needed for proper securement of the implant (710).

Figure 28:
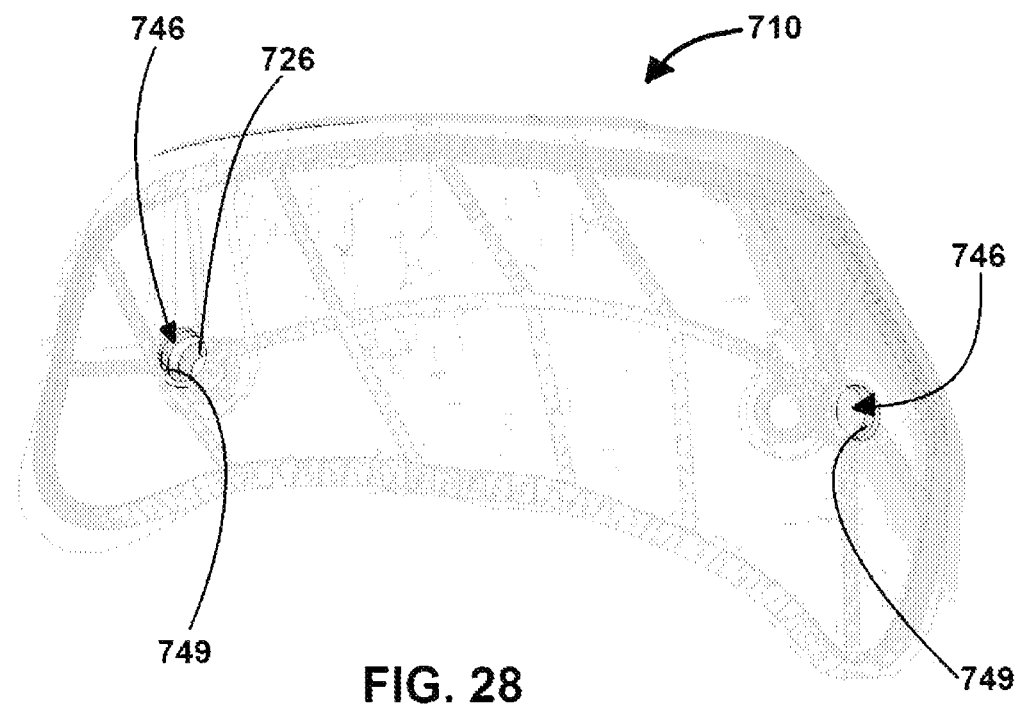
FIG. 28 is a top view of the implant of FIG. 24, wherein the plate is depicted translucently in order to better show the relationship between the biocompatible plate and the internal support frame.
Figure 29:
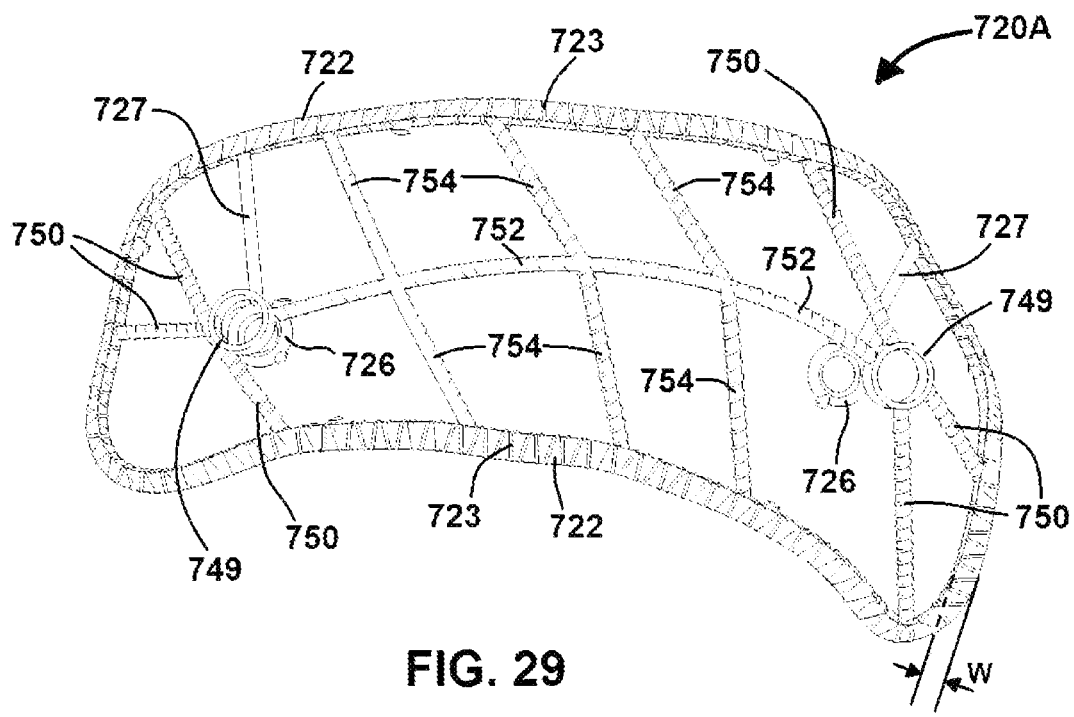
FIG. 29 is the same view as FIG. 28, with the biocompatible plate omitted.

Unlike the previously described implants that employ a standardized support frame (120) that is modified and manipulated as needed for a particular implant, supraorbital implant (710) includes not only a customized plate (712) but also a custom-fabricated support frame (720A) made to meet the needs of a specific patient. In general, however, and as best seen in FIGS. 28 and 29, the wire mesh support frame (720A) includes a continuous, internal base rim (722) that traverses a continuous, closed loop and has a shape approximating that of the outer perimeter of the plate (712) at the bone-facing surface (717) thereof. The support frame (720A) is configured such that, in the final implant (710), the base rim (722) will be located just inside the perimeter of the plate (712). In some embodiments, the outermost edge of the base rim (722) of the support frame (720A) is spaced no more than 5 mm, or no more than 3 mm, or no more than 2 mm from the outer perimeter of the plate (712).

The surface of the base rim (722) is also textured rather than smooth in order to not only improve cement adherence to the base rim (722), but also to help prevent fracturing of the cement along a fracture surface extending along the rim (722). In fact, any portions of the various support frames described herein can be textured rather than smooth for the same reasons. The surface of the wire rim (722) can be textured using any of a variety of patterns so as to provide an uneven surface. In the embodiment shown, a spiral ridge (723) extends about and along the length of the base rim (722). In this particular embodiment, the base rim (722) has a width (W) (see FIG. 29) of between about 0.7 and about 1.4 mm, and the spiral ridge has a height of about 0.1 mm. The base rim (722) in this embodiment also has a triangular cross-section in order to allow for thinning of the plate around its perimeter for a smoother transition between the implant and surrounding bone. Thus, base rim (722) is thickest on its interior side.

As noted previously, eyelets (726) are located within the boundary of the outer perimeter of the plate, and therefore are located within the interior of the base rim (722). Each eyelet is supported by a single wire strut (727) that extends inwardly from the rim (722). By supporting each eyelet (726) with a single strut (727), the eyelets (726) can be repositioned not only at the time of molding, but also at the time of implantation of the implant in a patient (either purposefully or as a result of fastening the implant in place). While the support frame (720A) is fabricated in a precise manner, in some instances it will be necessary to make minor adjustments to the position of the eyelets (726) so that they are properly positioned within the mold for the plate (712). Thus, while the support frame (720A) is custom fabricated to meet the needs of a particular patient, the support frame nevertheless can be modified and adjusted prior to molding of the plate (712) about the support frame (720A).

Cylindrical sleeves (749) that line the bores (746) in the final implant (710) are formed integrally with the support frame (720A). As best seen in FIG. 29 each cylindrical sleeve (749) is elevated above an eyelet (726) and supported by three support arms (750) that extend upwardly and inwardly from the base rim (722) to the cylindrical sleeve (749), supporting the sleeve (749) at various points arrayed about its perimeter. A support girder (752) also extends between the cylindrical sleeves (749), upwardly curving away from each of the sleeves (749). A series of lateral struts (754) extend upwardly and inwardly from the base rim (722) to the support girder (752), further maintaining the elevated position of the girder (752) and the cylindrical sleeves (749). In the embodiment shown, the support arms (750), support girder (752) and lateral struts (754) are textured similar to base rim (722), and therefore each includes a spiral ridge extending about and along the length of these wire members.

Together, the support arms (750), support girder (752) and lateral struts (754) not only support the cylindrical sleeves (749) at their proper position, these additional wire members and sleeves provide an interior scaffold for supporting the interior region of the plate (712). The outer surface (718) of the plate (712) is generally convex in shape, and the interior scaffold has a similar shape, with the support girder being curved in one or more directions along its length. This interior scaffold structure provides increased rigidity and support for the plate (712), particularly in the central region of the plate (712). For example, the support arms (750), support girder (752) and lateral struts (754) are configured to be located just below the outer surface (718) of the plate (712), e.g., no more than 5 mm, or no more than 3 mm, or no more than 2 mm below the outer surface (718).

While the support frame (720A) can be fabricated as shown in FIG. 29 with no further modification prior to molding of the plate (712) thereabout, in some instances it is advantageous to initially manufacture the support frame such that additional support is provided for the eyelets (726). The additional support not only can facilitate the manufacturing process, but can also provide additional options at the time of molding.

For example, support frame (720) depicted in FIGS. 30-32 can first be custom fabricated to approximate the desired shape of the plate (712) of the final implant, and then modified and manipulated to provide the modified support frame (720A) described above. In particular, the unmodified support frame (720) includes three additional wire struts (729A, 729B, 729C) connecting the eyelets (726) to the base rim (722). The additional wire struts (729A-C) extend inwardly from the base rim (722) to the eyelets (726), supporting each eyelet (726) at various points arrayed about its perimeter. These additional wire struts (729A-C) not only provide additional support for the eyelets during fabrication of the support frame (720), they also allow for additional options for adjusting the position of the eyelets (726) prior to molding.

Despite the ability to precisely fabricate the support frame (720) to match plate (712) to be molded thereabout, as well as the ability to precisely fabricate the mold for the plate (712), it may be necessary to adjust the location of the eyelets (726) to ensure that they are properly located within the mold without having to deform the base rim (722) or the interior scaffold structure located within the perimeter of the base rim. For example, if one of the eyelets (726) needs to be moved closer to the lower edge of the base rim (722) in the view depicted in FIG. 30, the wire strut (727) for that eyelet would need to be cut in order to allow for such adjustment else the upper edge of the base rim (722) would have to be deformed inwardly to accommodate the adjustment. In this instance, rather than using wire strut (727) as the single strut supporting the eyelet, one of the additional wire struts (729A-C) would be used instead (e.g., wire strut (729A)). The other wire struts (e.g., 727, 729B, 729C) are removed prior to placing the support frame (720) in the plate mold. Thus, although each eyelet (726) is supported from the base rim by multiple struts (727, 729A, 729B, 729C), all but one are removed prior to molding the plate around the support frame. By using only a single strut for each eyelet (726) in the final implant, the eyelets are able to be adjusted prior to implantation and/or move during the securement process without cracking the cement plate. It will also be understood that, when necessary for alignment of a cylindrical sleeve (749) with its underlying eyelet (726), one or more of the support arms (750) for that sleeve may be removed as necessary to allow for adjustment of the sleeve position.

Figure 26:
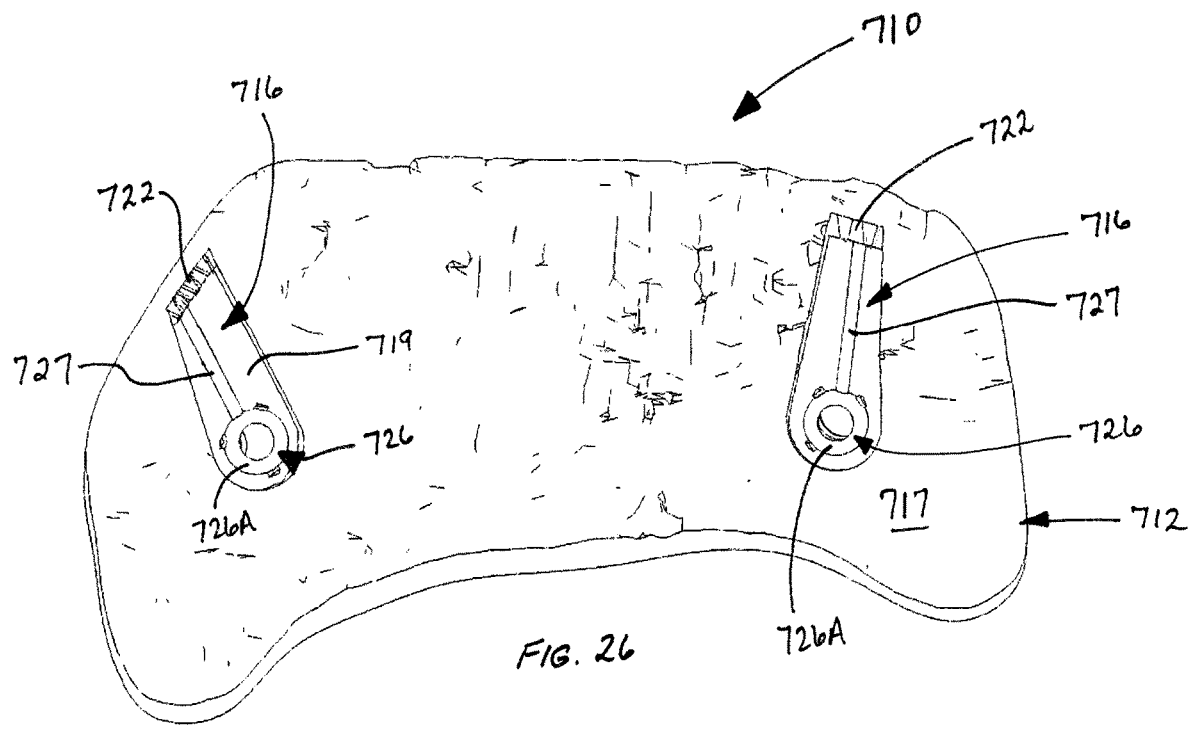
Figure 27:
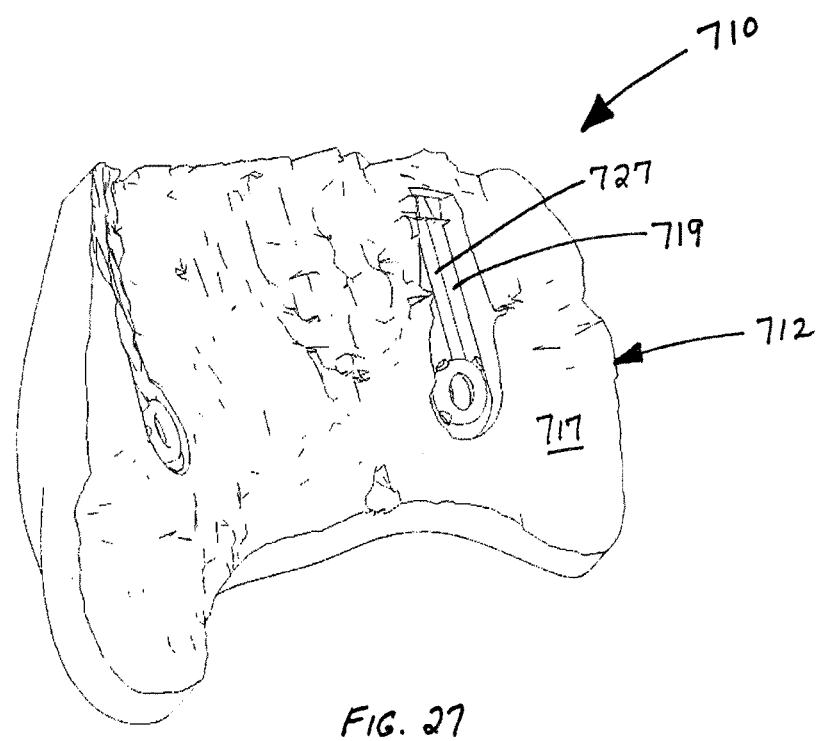

As mentioned previously, following molding of the plate, the eyelets (726) are located within cavities (716) provided in the bottom (bone-facing) surface (717) of the plate (712), at the base of the bores (746) that extend through the thickness of the plate (712) (see FIG. 26). Each of the eyelets (726), at least a portion of their respective supporting wire strut (727) and, optionally, a portion of the base rim (722) adjacent the wire struts (727), are free of cement, such that the eyelets (726) and at least a portion of the struts (727) float within their respective cavities (716). In order to form the cavities (716) and prevent cement from covering the eyelets and other portions of the support frame, guards are positioned over the portions of the support frame that are to remain cement-free prior to molding the plate (712). The guards act as a barrier between the cement and the eyelets, wire struts and portion of the base rim during molding, thus preventing the cement from hardening over these regions and forming the cavities (716).

In the example shown in FIGS. 33-35C, the guards comprise silicone covers (760) configured to be slid over an eyelet (726), its wire strut (727) and a portion of the base rim (722) at the juncture of the strut (727) and the base rim. The silicone cover (760) includes a rounded end configured to be slid over an eyelet (726) and a tapered portion configured to be slid over the wire strut (727) (i.e., retention arm) and a portion of the base rim (722) where the wire strut (727) connects to the base rim (722). The cover (760) is slit along one side and a portion of the opposing side in order to provide access to an interior pocket (762) for receiving an eyelet (726), wire strut (727) and portion of the base rim (722) therein. As with the silicone sleeve (142) described previously, by forming the cavities (716) using a guard that is applied over the eyelet and its retention arm (i.e., wire strut (727)) prior to molding the plate, the cavity (716) will be deeper than the thickness of the eyelet (726) and wire strut (727) located therein, and will also be wider than the outer diameter of the eyelet and wire strut. In this manner, the cavity (716) is sized such that the eyelet (726) and wire strut (726) is not in contact with the walls of the cavity. As also seen in FIG. 26 (as well as FIG. 23), the cavity can be tapered in width, with the largest width portion of the cavity adjacent the retention eyelet (i.e., the width narrows towards the base rim (722)).

Figure 33:
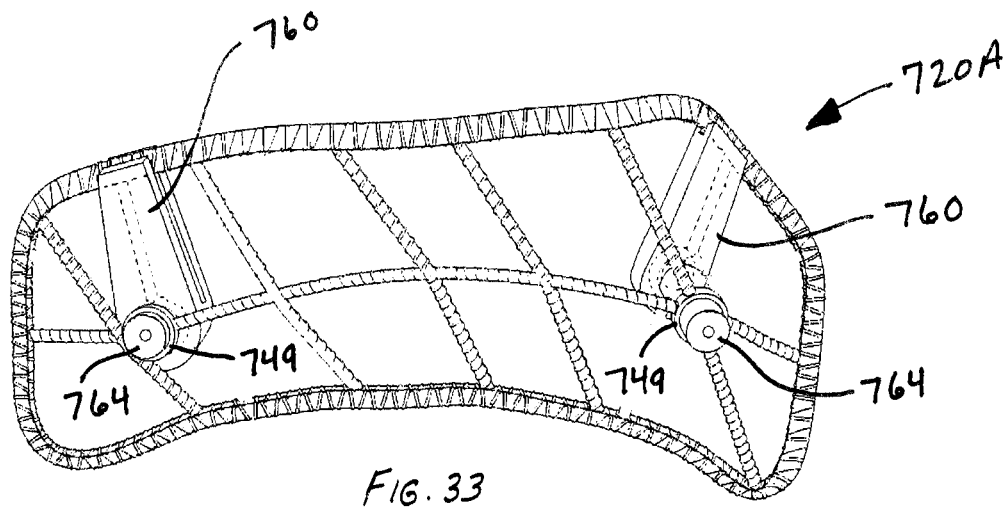
Figure 34:
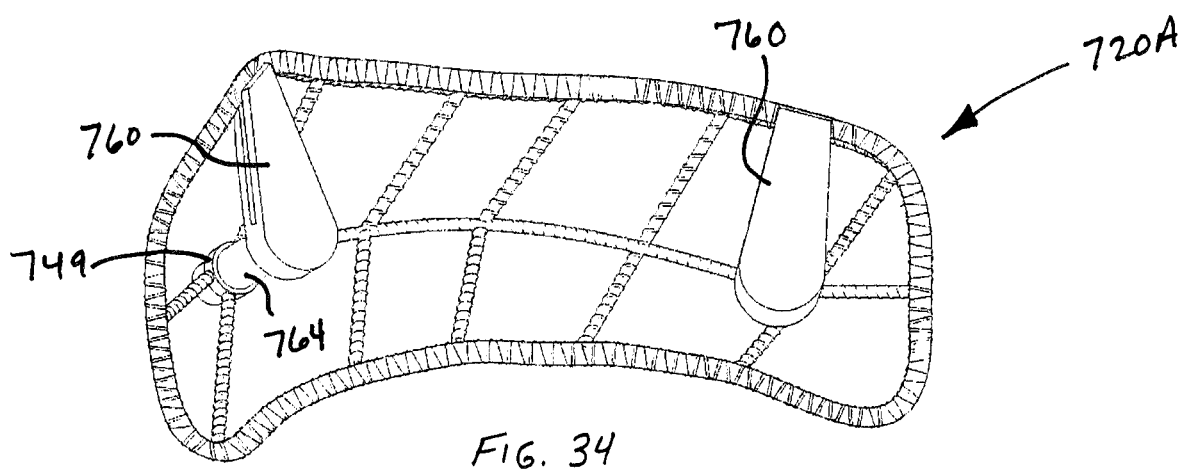
FIG. 34 is a bottom view of the assembly shown in FIG. 33.
Figures 35A, 35B, 35C:
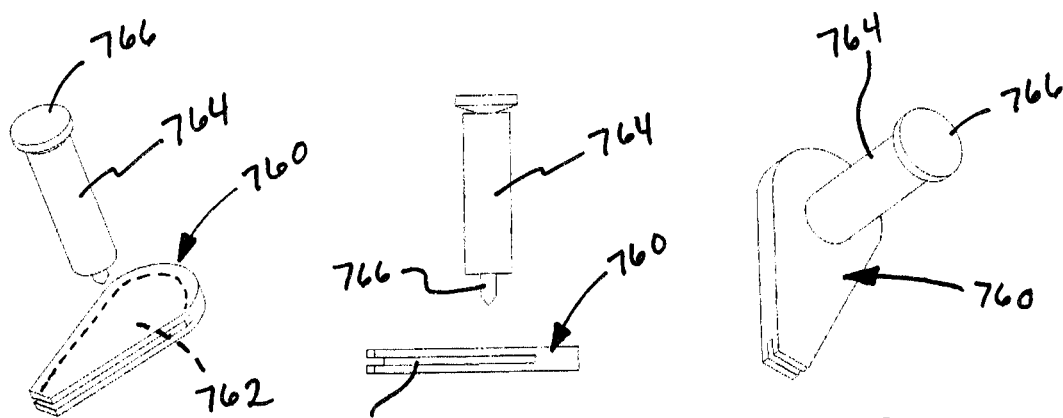
Figure 39:
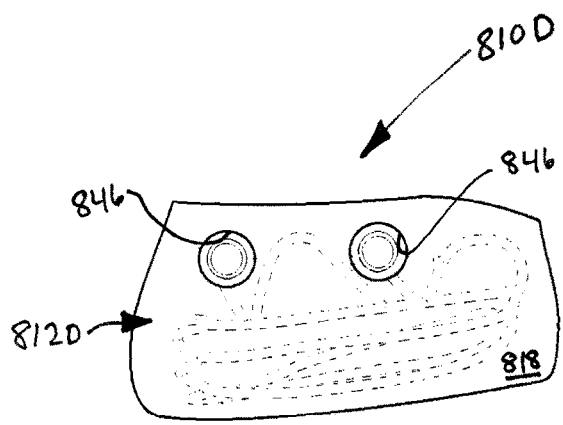

The guard assemblies also include a silicone rod (764) for forming the bores (746) during plate molding. As shown in FIGS. 33 and 34, the silicone rods (764) are inserted into the sleeves (749) of the support frame (720A) in order to not only prevent cement from entering the interior of the sleeves (749) but also to leave behind the bores (746) following cement hardening. The guard rod (764) may be integrally formed with the guard cover (760) as a single unit. Alternatively, as shown in FIGS. 35A-C, the rod (764) comprises a separate structure that is secured to the cover (760) by a pin (766) extending through the interior of the rod (764) into the cover (760). After the cover has been positioned about the eyelet (726) and the rod (764) inserted into the corresponding sleeve (749), abutting against the outer surface of the cover (760), the pin is inserted through the rod and into the cover (760), thereby holding the end of the rod (764) in contact with the surface of the guard cover (760). It will be understood that the rod (764) can be hollow, with an interior diameter slightly smaller than the outer diameter of the shaft of the pin (766) in order to better retain the pin within the rod. In addition, the pin (766) is not shown in FIGS. 33 and 34. The guard assembly comprising cover (760) and rod (764) shown in FIGS. 35A-35C can also be used to form the cavities (516) and bores (546) in implant (510) of FIGS. 22 and 23.

Once the guard assemblies are in place as shown in FIGS. 33 and 34, the support frame (720A) is placed into a mold for the plate (712). One the molding process is complete, the guard assemblies are removed, each leaving behind a cement-free cavity (716) and bore (749) through which a bone screw or other fastener can be inserted.

FIGS. 36-48B depict various aspects of the six-section mandibular implants (810A-E). These implants can be used, for example, to augment a patient's mandible. In the case of reconstruction of the entire lower part of the mandible, all six implants (810A-E) are employed. In other instances, less than all of the implants are necessary. Of course it will be understood that any number, sizes and configurations of mandibular implants may be fabricated according to the teachings herein, such as less than or more than six implants configured to span the length of the mandible. In addition, while the mandibular implants (810A-E) are depicted as separate, unconnected structures, they can alternatively be connected to one another (e.g., by one or more deformable connecting wire members).

Each mandibular implant (810A-F) is similar to the paranasal and supraorbital implants in that it includes a biocompatible plate and an internal wire mesh support frame, using the internal fastening arrangement similar to the supraorbital implant (710) rather than the external fastening used in the paranasal implant (110). The structure of the implants (810A-F) will be described in detail with reference to fourth mandibular implant (810D). This implant generally comprises a biocompatible plate (812D) and an internal support frame (820D) (see FIG. 40). The support frame includes a pair of fastening points comprising eyelets (826) located within the bounds of the outer perimeter of the plate (see FIG. 39). The retention eyelets (826) are located within cavities (816) provided in the bottom (bone-facing) surface (817) of the plate (812D), at the base of bores (846) that extend through the thickness of the plate (812D) between the upper (i.e., outer) and bottom (bone-facing) surfaces (818, 817) of the plate. Each eyelet is connected to the internal portion of the support frame (820D) by a retention arm comprising a single wire strut (827) attached to a wire member of the support frame.

Each of the eyelets (826), the wire struts (827) and the portions of the wire member adjacent the wire struts (827) are free of cement, such that the eyelets (826) and struts (827) float within their respective cavities (816). Thus, the cavities (816) are slightly deeper than the thickness of the eyelets (826) and the diameter of the struts (827) such that each eyelet (826) and strut (827) is spaced away from the bottom surface of their respective cavities (816). The bottom face, i.e., the bone-facing surface of each eyelet is approximately flush with the bone-facing surface (817) of the plate prior to implantation. Alternatively, the upper face of one or both eyelets can be positioned on the bottom surface of its cavity (816) but is still free to slide across that bottom surface so as to allow movement of the eyelet without risk of cracking the plate material. In addition, in alternative embodiments the bottom face of each eyelet extends beyond the bottom surface (817) of the plate prior to implantation (i.e., is not flush therewith), or is located below the level of the bottom surface (817) of the plate (i.e., the cavities are deeper than those depicted in the figures). It should also be pointed out that the eyelets and their respective cavities are not shown in FIGS. 37 and 38.

Unlike the supraorbital implant (710), the bores (846) of the mandibular implants are not lined using a cylindrical sleeve, as the thickness of the cement plate is smaller. However, it will be understood that the support frames of the mandibular implants can be modified in order to provide such protective linings within the bores (846).

Since each mandibular implant (810A-F) is sized, shaped and configured to meet the specific needs of a specific patient, the shape and dimensions of plate (812D) as well as the other plates shown in the drawings is merely exemplary. In general, the outer surface (818) is smooth and curved to not only match surrounding bone and other tissue, but also to provide an aesthetically pleasing appearance. The goal of the mandibular implants (810A-F) is to mimic the appearance of a normal mandible, particular the lower portion thereof. The bottom, or bone-facing surface (817) of the cement plate is contoured to match the shape of the underlying bone and other tissue (where bone and other tissue is present), and, where bone is missing, avoid any underlying tissue to be protected by the plate. In addition, the location of the eyelets (826), and hence the bores (846), is chosen to not only adequately secure the implant (810A-F) in place, but also to ensure that there is sufficient bone for receiving a bone screw or other fastener.

Mandibular implants (810A-F) are secured in place similar to the previously described implants. Once the implant (810A-F) is properly positioned in a patient, a bone screw or other fastener is inserted into the plate through each of the bores (846), through the underlying eyelets (826) and into the underlying bone. As each bone screw is threaded into the underlying bone, the eyelet (826) through which it extends will be pulled toward the bone until the bone-facing surface of the eyelet is flush against the bone. The wire strut (827) to which the eyelet is attached will typically flex away from its cavity (816) to some extent, and perhaps laterally within the cavity as the bone screw is tightened. However, the cement of the plate (812D) generally will not crack due to the fact that the cement does not cover the eyelet (826) or its supporting strut (827). While two bone screws driven through the bores and eyelets into underlying bone will usually be sufficient to secure the implant (810A-F) in place, it will be understood that more than two eyelets and associated bores may be provided on the implant—particularly for larger implants and/or when there is some uncertainty ahead of time of the optimal fastening location, as described above with respect to supraorbital implant (710).

Like supraorbital implant (710), each of the mandibular implants (810A-F) includes not only a customized plate (812) but also a custom fabricated support frame made to meet the needs of a specific patient. In general, and as best seen in FIGS. 40 and 43A-E, the wire mesh support frame (820D) comprises a skeletal-like scaffold for supporting the cement plate molded thereabout, and includes a plurality of lengthwise-extending, curved support ribs (856) that are joined to one another at their respective ends by curved side struts (857). The Support ribs (856) and side struts (857) together form a bowl-shaped scaffold for internally supporting the cement plate. The bowl-shaped scaffold has a shape approximating that of the outer perimeter of the plate (812).

Figure 40:
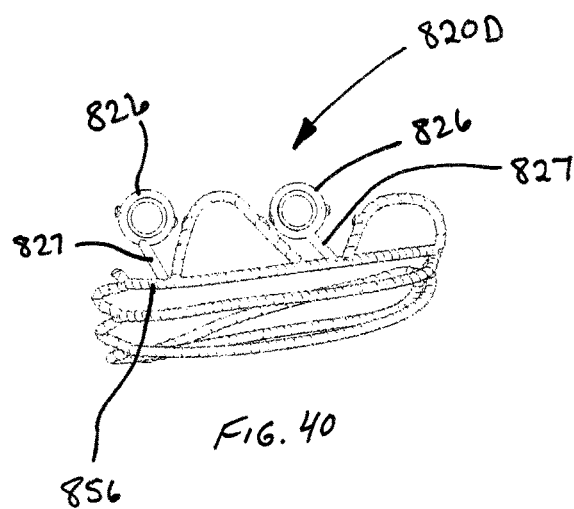
FIG. 40 is a front view of the support frame used in the mandibular implant section of FIG. 38.
Figure 41:
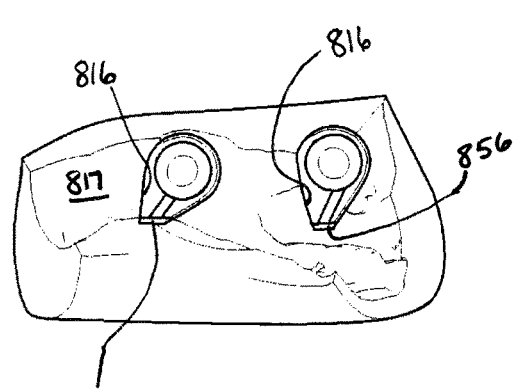
Figure 42:
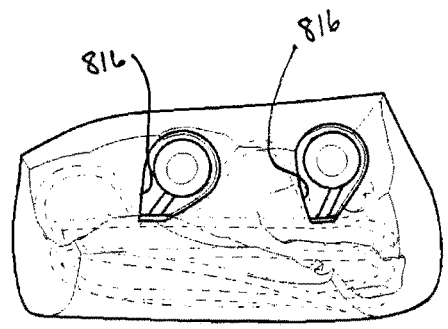
Figure 44A:
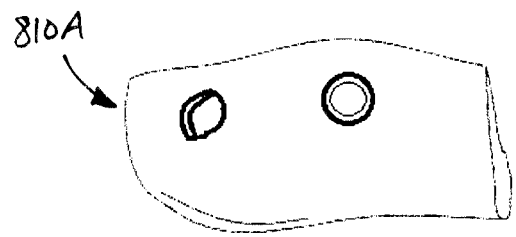
FIGS. 44A-B, 45A-B, 46A-B, 47A-B and 48A-B depict the other five mandibular implant sections of FIG. 36 and their respective, unmodified support frames.
Figure 44B:
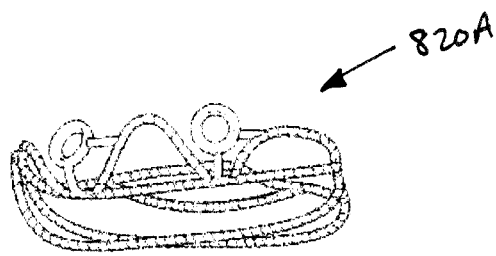
Figure 45A:
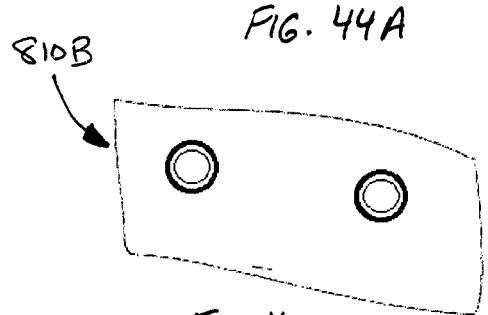
Figure 45B:
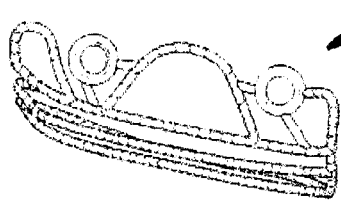
Figure 46A:
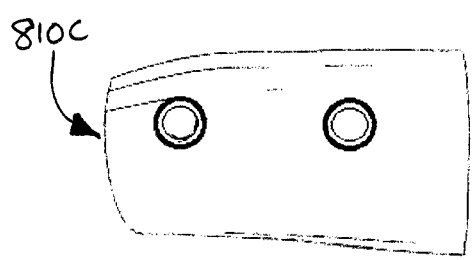
Figure 46B:
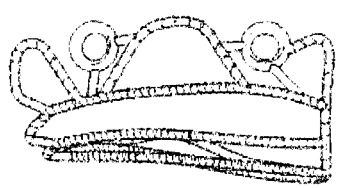
Figure 47A:
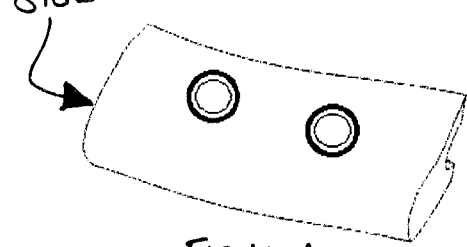
Figure 47B:
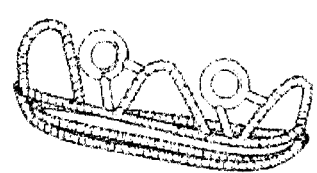
Figure 48A:
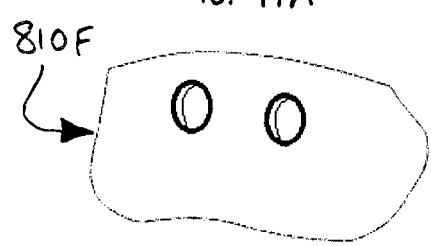
Figure 48B:
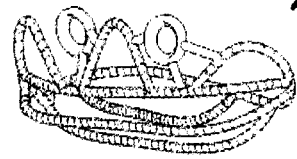
Figure 53:
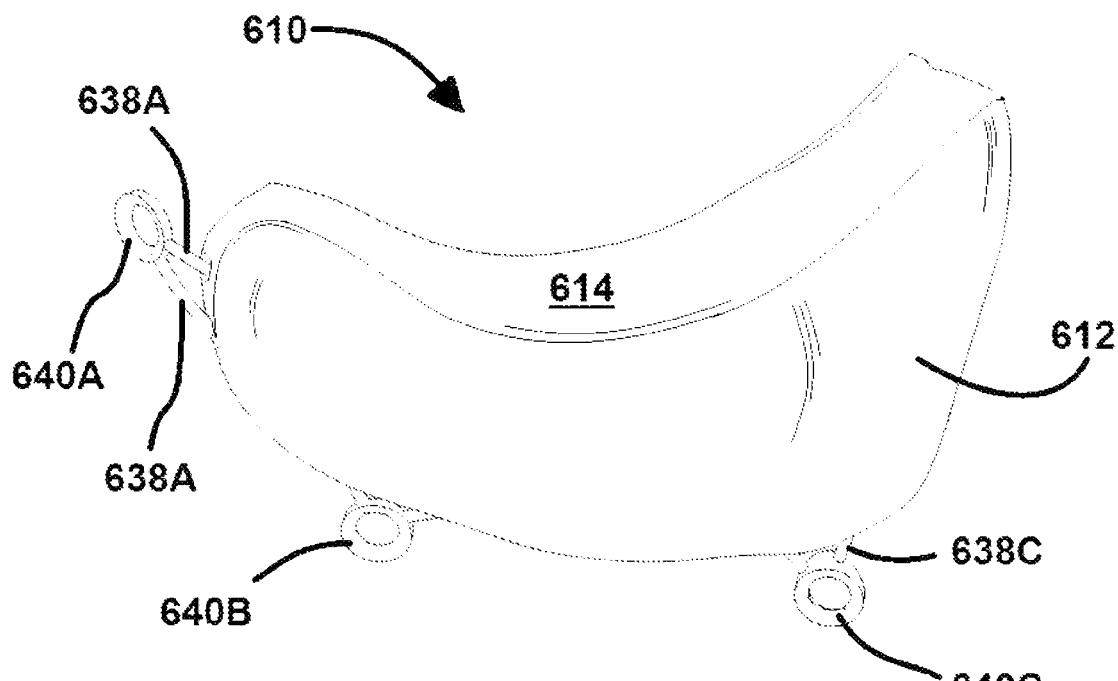
FIG. 53 is an orthogonal view of an embodiment of a zygoma implant.

Like the support frame of implant (710), although the support frame (820D) can be fabricated as shown in FIG. 40 with no further modification prior to molding of the plate (812D) thereabout, in some instances it is advantageous to provide additional support for the eyelets (826) during manufacture of the support frame. The additional support not only facilitates manufacturing, but also provides additional options at the time of molding. Thus, as initially fabricated, and as depicted in FIGS. 43A-E, support frame (820D) further includes three curved support arms (858A, 858B, 858C) extending upwardly away from the upper-most support rib (856). It will be understood that one or more of these support arms can be straight, rather than curved, depending on the desired shape of the implant and/or position of the retention eyelets. The first support arm (858A) is connected directly to one of the eyelets (826), while the second and third support arms (858B, 858C) are generally U-shaped, and are connected to the upper-most support rib (856) at each end of the support arms (858B, 858C). The wire strut (827) connecting each eyelet to the rest of the support frame extends between the eyelet and the upper-most support rib (856), as shown, with the second curved support arm (858B) extending upwardly between the eyelets (826). In addition, as initially fabricated, each eyelet is further connected to a pair of the curved support arms (858A, 858B, 858C). In the exemplary embodiment shown in FIGS. 43A-E, one eyelet (826) is directly connected to the first support arm (858A) and is connected to the second support arm (858B) by an additional wire strut (829) extending between the eyelet (826) and the second support arm (858B). The other eyelet (826) is connected to the second and third support arms (858B, 858C) by a pair of additional wire struts (829) extending between the eyelet (826) and the second and third support arms (858B, 858C). Depending on the desired shape of the implant, the first support arm (858A) instead can be configured similar to third support arm (858C) (i.e., connected to the upper-most support rib (856) at each end of the support arm (858A) and an additional wire strut (829) extending between the adjacent eyelet (826) and the first support arm (858A)). Alternatively, the third support arm (858C) can be configured similar to first support arm (858A) (i.e., connected directly to the adjacent eyelet (826)).

Although each eyelet (826) is supported, directly or indirectly, from the upper-most support rib (856) by multiple struts (827, 829), all but one are removed prior to molding the plate around the support frame. Once again, by using only a single strut for each eyelet (826) in the final implant, the eyelets are able to be adjusted prior to implantation and/or move during the securement process without cracking the cement plate. Thus, prior to inserting the support frame (820D) into the plate mold, first support arm (858A) and additional wire struts (829) are removed (e.g., cut away) from the support frame to provide the support frame (820D) in the configuration shown in FIG. 40.

As also seen in the figures, the surface of the curved support ribs (856), curved side struts (857) and support arms (858A, 858B, 858C) are textured rather than smooth in order to improve cement adherence and help prevent fracturing of the cement along a fracture surface. The surfaces can be textured using any of a variety of patterns so as to provide an uneven surface, such as the spiral ridges shown.

In order to form the cavities (816) in the bottom (bone-facing) surface (817) of the plate (812), guard assemblies configured similar to those shown in FIGS. 35A-C) are positioned over the portions of the support frame that are remain cement-free prior to plate molding. As before, the guard assemblies not only act as a barrier between the cement and the eyelets and other portions of the support frame during molding process, the guard assemblies also form the cavities (816). Similarly, the rod portions of the guard assemblies are positioned in the plate mold so as to form the bores (846) immediately above the eyelets (826).

FIGS. 44A-48B depict the other mandibular implants (810A-C, 810E and 810F) and their respective support frames (820A-C, 820E and 820F). It will be understood that the support frames are shown in their as-fabricated configuration. Prior to plate molding, the support frames are modified such that only a single wire strut connects each eyelet to the remainder of the support frame, as described above.

FIGS. 49-52 depict yet another alternative embodiment of an implant (910) similar to supraorbital implant (710). In this instance, the support frame (920) includes an external rim located about at least a portion of the outer perimeter of the plate (912). In the embodiment shown, the external rim comprises first and second external rims (970A, 970B) located along opposing sides of the implant (910). External rims (970A, 970B) are connected to an internal rim (922) located inside the plate (912). Internal rim (922) is configured similar to rim (722) of supraorbital implant (710), and is connected to the first and second external rims (970A, 970B) by a plurality of wire struts (972) extending between the rims (922, 970A, 970B) through the outer edge of the cement plate (912).

The external rims (970A, 970B) serve to provide a smooth transition between the biocompatible plate (912) and the surrounding bone, and therefore have a tapered cross-section as seen in FIG. 52. The external rims (970A, 970B) also elevate the plate (912) above the surface of the underlying bone and tissue following implantation, as also seen in FIG. 52.

In the particular embodiment shown in FIGS. 49-52, external rim (970A) extends along the first long edge of the plate (912) while external rim (970B) extends along the second long edge of the plate (912) located opposite the first long edge. It will be understood, however, that additional external rims can be provided, including a single external rim extending around the majority or even the entirety of the outer periphery of the plate (912) (as one continuous rim, or as two or more rim sections arrayed about the outer periphery of the plate).

As best seen in the cross-sectional view of FIG. 52, in the depicted embodiment the external rims (970A, 970B) abut against the outer peripheral edge of the plate (912), with little or no space (less than 0.5 mm, less than 0.3 mm or less than 0.1 mm) between the inner surface (971) of the external rim and the outer peripheral edge of the plate (912). The upper surface (973) of the external rim slopes downwardly and outwardly away from the upper (i.e., outer) surface of the plate (912) such that a smooth transition is provided between the plate (912) and the external rims (970A, 970B) where their respective upper surfaces (918, 973) meet. The external rims (970A, 970B) taper to a thin outer edge to as to provide a smooth transition between the external rims and the surrounding bone following implantation. When the plate is made of a breakable or relatively fragile material such as cement, it may not be feasible to provide such a thin outer edge for a smooth transition between implant and bone.

The height of the external rims (970A, 970B) at the inner surface (971) thereof is slightly greater than that of the plate (912) at its outer peripheral edge such that, when viewed from the side (FIG. 52), the external rims (970A, 970B) extend below the outer edge of the bottom (bone-facing) surface (917) of the plate (912). By configuring the external rims (970A, 970B) so as to extend below the plate at its peripheral edge, the bottom surface (975) of the external rims will rest against the surrounding bone following implantation, while elevating the plate (912) elevated slightly (0.1-1.0 mm, or 0.1-0.5 mm, or about 0.2 mm) above the surface of the bone or other tissue underlying the plate (912). As a result, tension on the implant (e.g., from small bone structures not distinguishable from the CT-scan due to resolution) will be directed on the external rim (970A, 970B) rather than the plate (912), thereby helping to prevent damage to the plate (912) (e.g., when the plate is made of a cement and the external rim is made of metal such as titanium or titanium alloy).

As also seen in the cross-sectional view of FIG. 52, like the configuration of implant (710), each of the internal retention eyelets (926) is attached to the support frame (920) by a single, deformable wire strut (927), with the eyelets and their retention arms (i.e., wire struts (927)) floating within cavities (916) provided in the bottom (bone-facing) surface (917) of the plate (912), at the base of bores (946) extending through the thickness of the plate. Thus, when a bone screw (944) is inserted into a bore (946) and through the associated eyelet (926) into bone, the eyelet will be pulled toward the bone until the bone-facing surface of the eyelet (926) is flush against the bone. The wire strut (927) to which the eyelet is attached will typically flex away from its cavity (916) to some extent, thus allowing the bone-facing surface of the eyelet (926) to be in firm contact with the bone, while the bone-facing surface (917) of the plate (912) remains elevated away from the bone.

The support frame (920) can be fabricated in any of the variety of manners mentioned previously, with the external rims (970A, 970B) formed integrally with the rest of the support frame (920). As best seen in FIG. 50, the external rims (970A, 970B) are located in spaced-apart relationship from the internal rim (922) by the plurality of wire struts (972) extending therebetween. The wire struts (972) maintain the desired spacing between the external rims (970A, 970B) and the internal rim (922), such that cement (or other plate material) can be molded between the external rims (970A, 970B) and the internal rim (922). In some instances, these struts (972) are also deformable (e.g., bendable or flexible) to allow for adjustment of the position of the external rims (970A, 970B) within the mold for the plate (912) and/or at the time of implantation.

In some embodiments (not shown), particularly when it is desired to allow for adjustment of the external rims (970A, 970B) at the time of implantation, the wire struts (972) connecting the internal and external rims extend out of the plate from open internal cavities through enlarged apertures, similar to the apertures (115) and cavities (116) of paranasal implant (110). As with the paranasal implant (110), in these embodiments both the aperture and the cavity are larger in diameter than the wire strut (972) extending therefrom, such that the wire strut (972) is not in contact with (or has only minimal contact with) the plate material. By providing such internal cavities and oversized apertures, wire struts (972) can flex or even be bent so as to allow for movement of the external rims (970A, 970B) during implantation and/or adjustment of the external rims for better fit without risk of cracking the plate material—particularly vertical adjustment and/or movement of the external rims such that the spacing between the bone-facing surface (917) of the plate (912) and the underlying bone or other tissue is altered.

Apart from the external rims (970A, 970B) and associated wire struts (972), the support frame (920) of implant (910) is similar to support frame (720), and therefore further includes cylindrical sleeves (949) elevated above each eyelet (926) and supported by three support arms (950) that extend upwardly and inwardly from the internal rim (922) to the cylindrical sleeve (949). A support girder (952) extends between the cylindrical sleeves (949), upwardly curving away from each of the sleeves (949), with a series of lateral struts (954) that extend upwardly and inwardly from the internal rim (922) to the support girder (952). It will be understood that external rim(s) can be provided on any of the other support frames and implants described herein.

FIGS. 53-59 depict a zygoma implant (610), which is configured to be secured to patient's zygomatic and maxilla bones, as depicted in FIG. 1. Thus, zygoma implant (610) is particularly adapted for zygoma reconstruction or cosmetic alteration of the same region. Zygoma implant (610) comprises a biocompatible plate (612) and an internal wire mesh support frame (620). The support frame (620) is constructed similar to the internal support frames (820A-F) of the mandibular implants described above, but employs externally spaced-away retention eyelets (similar to paranasal implant (110)) rather than internal retention eyelets located within the perimeter of the plate.

As with the previously described implants, zygoma implant (610) is secured to surrounding bone using fasteners such as bone screws driven through fastening points in the form of retention eyelets (640A, 640B, 640C). While three such retention eyelets are depicted, in some instances it will only be necessary to use two of the three retention eyelets. Alternatively, the implant can be configured to provide more than three retention eyelets, with all or only some of those eyelets actually used during implantation. As before, unused eyelets and their retention arms can be removed prior to implantation.

The zygoma implant (610) includes an internal wire mesh support frame (620), with the plate (612) molded about the support frame. Any of the previously described materials and compositions can be used to mold the plate (612) about the support frame (620), such as a monetite-forming, hydraulic cement composition. The implant (610) can be customized based on the needs of a particular patient, particularly the size and configuration of the biocompatible plate (612) and the location of the retention eyelets (640A, 640B, 640C). Thus, the particular zygoma implant (610), including the plate (612) and support frame (620) shown is merely exemplary.

Figure 54:
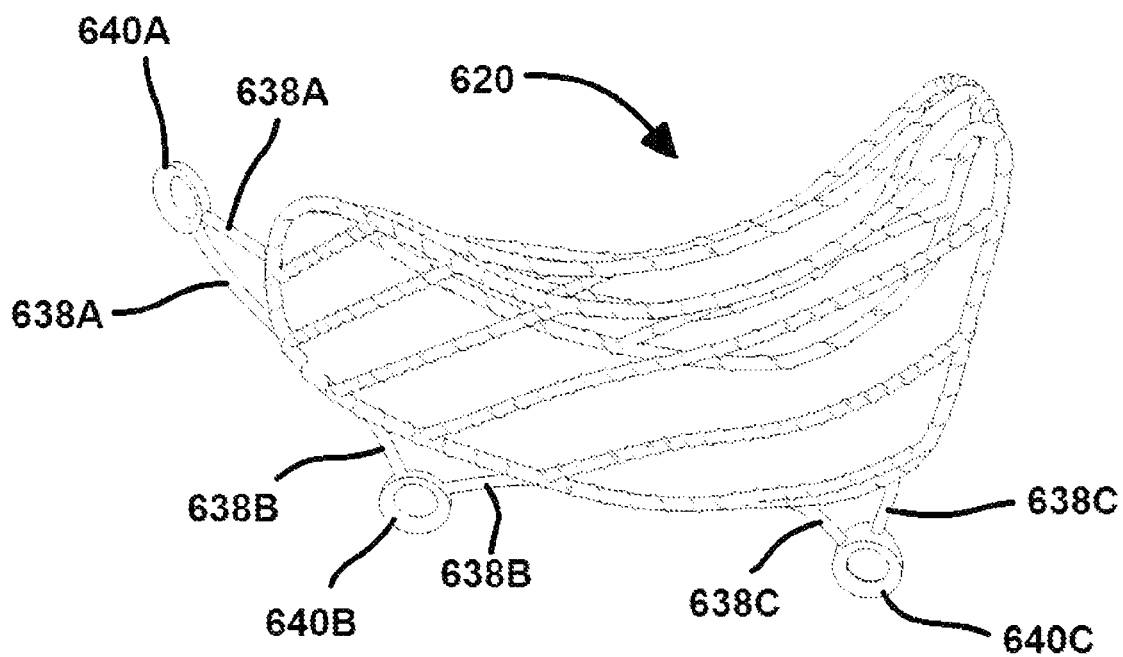
FIG. 54 is an orthogonal view of the support frame of the zygoma implant of FIG. 53.
Figure 59:
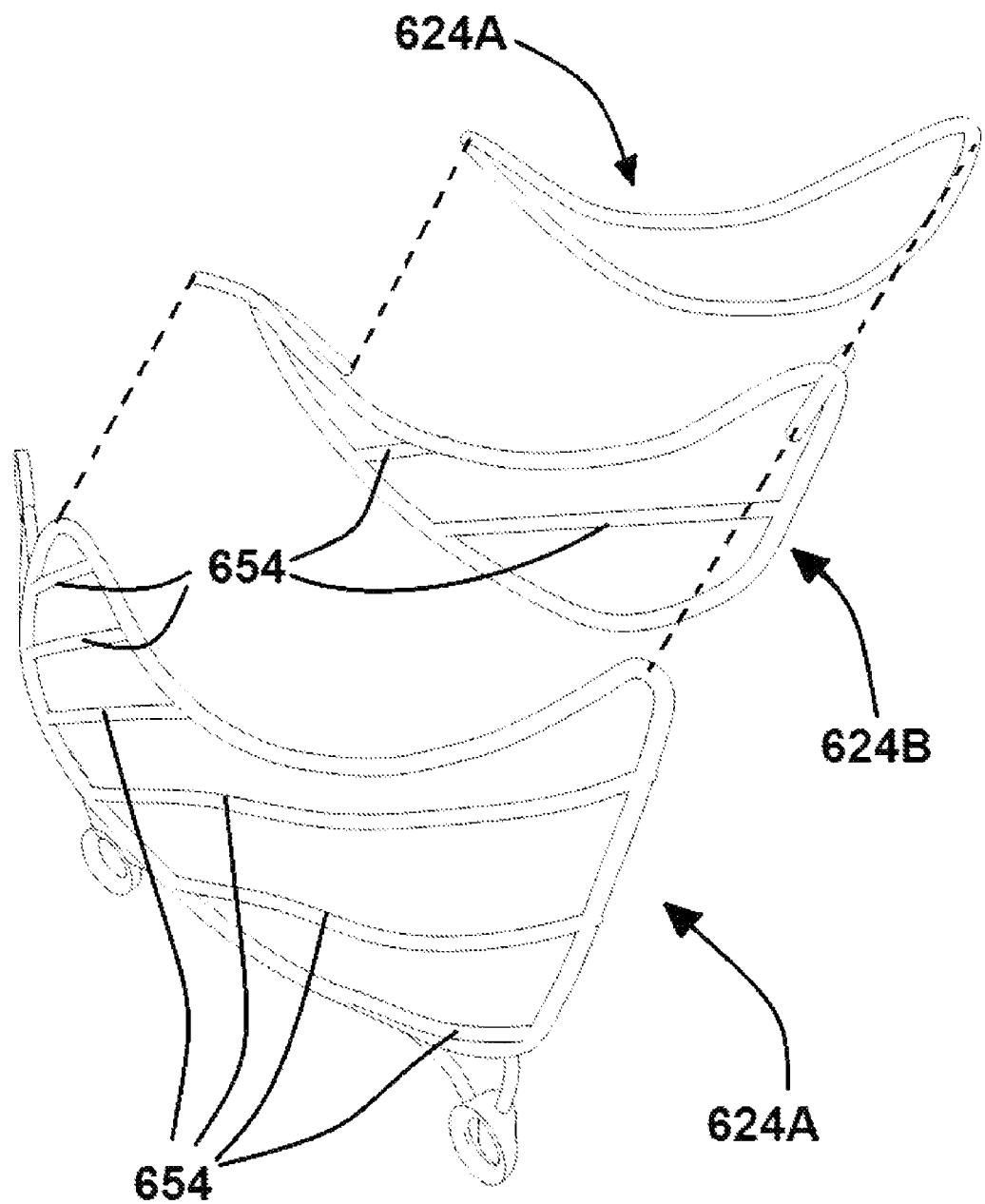
FIG. 59 is an exploded view of the support frame of the zygoma implant of FIG. 53, wherein the surface texturing has been omitted for purpose of clarity.

Each retention eyelet (640A, 640B, 640C) is provided at the external ends of a pair of retention arms (638A, 638B, 638C), each of which extends out of the outer sidewall (614) of the plate (612) through an aperture (615) (see FIG. 57A). As seen in FIGS. 54, 55 and 57, retention arms (638A, 638B, 638C) are affixed to and extend away from a first rim (624A) located within the plate (612). As with the previous embodiments, while implant (610) is custom fabricated to meet the needs of a particular patient, the retention arms (638A, 638B, 638C) also can be deformed (e.g., bent, including twisted and/or flexed) at the time of implantation in order to ensure a proper fit. In order to reduce the risk of cracking of the plate (612) when the retention arms are deformed at the time of implantation, the plate (612) is molded about the mesh support frame such that retention arms (638A, 638B, 638C) as well as a portion of the first rim (624A) adjacent the retention arms is not covered by the plate material. Thus, not only do the retention arms (638A, 638B, 638C) extend out of the plate (612) through an aperture (615) that is larger in diameter than that of the retention arms, the retention arms also extend out of the plate from open internal cavities (616) provided in the plate material adjacent each aperture (615). As in the implant (110), both the aperture (615) and the cavity (616) are larger in diameter than the retention arm (638A, 638B, 638C) extending therefrom, such that the retention arms are not in contact with (or have only minimal contact with) the plate material. As before, the apertures (615) through which the retention arms (138A) extend are generally located adjacent the bottom surface (617) (the bone-facing surface) of the plate (612), and the apertures (615) and cavities (616) can be formed in the manner described previously (e.g., using cylindrical sleeves over the retention arms and a portion of the rim (624A) to which they are attached).

The wire mesh support frame (620) of the zygoma implant (610) comprises a skeletal-like scaffold for supporting the cement plate molded therebout. The support frame (620) includes a plurality of rims (624A, 624B, 624C) that are spaced apart and connected to one another in order to form the scaffold-like structure of the support frame. Together, the plurality of rims approximate the shape of the outer perimeter of the plate (612). Thus, any number of rims, having any desired shape can be used depending on the required shape of the implant. In the example shown, the support frame comprises a first rim (624A), a second rim (624B) and a third rim (624C), with these rims joined to one another by a plurality of connecting struts (638) extending therebetween. Each of the rims, like those described previously herein, traverses a continuous, closed loop, as shown. For larger outer rims such as the first and second rims (624A, 624B), one or more support ribs (654A, 654B) are provided for additional strength and rigidity, with each of these support ribs spanning across the interior of the rims (624A, 624B) as shown.

As with the supraorbital and mandibular implants, the surfaces of the rims (624A, 624B, 624C) as well as the support ribs (654A, 654B) and connecting struts (638) are textured in order to not only improve cement adherence to the support frame, but also to help prevent fracturing of the cement along a fracture surface. This texturing can be configured in the manner described previously with respect to the supraorbital implant (710).

The implants described above are exemplary of various craniofacial implants that can be fabricated in accordance with the teachings herein. Similarly constructed implants can be made for other craniofacial regions, as well as for treating bone defects elsewhere in a patient. In addition, two of more of the above-described implants can be combined, such as a combined supraorbital and zygoma implant. Such combinations can be fabricated by connecting the support frames of the two components (e.g., supraorbital and zygoma) external to their respective plates, or by joining the two support frames and molding a unitary plate about the combined support frame structure. In addition, any of the implants described herein can be divided into two or more smaller implant sections, which are optionally joined to one another external to their respective plates.

The various wire mesh support frames described above may be formed in a variety of ways such as by welding wire segments and eyelets to one another in the arrangements shown, by a molding process or by cutting (e.g., laser cutting), etching or stamping a flat sheet to form the wire segments and eyelets and thereafter bending the material in to the final shape. Alternatively, the support frame may be cut, etched, stamped, molded or otherwise formed from a biodegradable polymer such as polycaprolactone.

As yet another alternative, in some embodiments the support frame, as well as the mold negative for use in fabricating the mold for forming the plate, are manufactured using additive manufacturing techniques (sometimes referred to as 3D-printing). In particular, the support frames and mold negatives for the implants are manufactured in this manner so as to provide implants that are customized for each patient and the bone defect to be corrected. Any of a variety of additive manufacturing methods can be employed, including stereolithography, fused deposition modeling (also known as fused filament fabrication), selective laser sintering, selective laser melting, electron beam melting, and others known to those skilled in the art or hereafter developed. Selective laser melting is particularly useful in fabricating the support frame, particularly when the support frame is titanium, titanium alloy or other metals. Selective laser sintering is useful for fabricating the mold negative in polyamide, while fused deposition modeling is particularly useful for fabricating the mold negative from, for example, PLA or ABS.

The additive manufacturing of implants to precisely match a patient's bone defect (e.g., a cranial defect) comprises the steps of:

1. Obtaining computed tomography (CT-scan) or magnetic resonance (MRI) data from the patient.
2. Digitally creating an anatomical model of the bone defect to be treated.
3. Digitally generating the plate design to fit the bone defect, including, for example, locating retention eyelets for optimal placement of fasteners (e.g., bone screws) into adequate bone or other tissue surrounding the defect.
4. Digitally generating the support frame design based on the plate design and eyelet locations.
5. Digitally generating the mold design based on the plate design.
6. "Printing" the mesh support frame using the digital mesh support frame design (e.g., by selective laser sintering of titanium or titanium alloy).
7. "Printing" the mold negative using the digital mold design (e.g., using a fused filament fabrication "printer").
8. Fabricating a silicon mold from the mold negative.
9. Positioning the mesh support frame in the mold (e.g., in the manner described previously).
10. Molding the plate about the support frame (e.g., using a hydraulic cement composition, such as those described previously).

The above additive manufacturing process provides a number of advantages, including rapid fabrication of customized implants for each patient, including the ability to fabricate implants with complex and/or irregular geometries (including complex curved surfaces). The implants are more structurally sound (resist deformation), and aesthetically pleasing following implantation. In addition, the implants will require minimal adjustment by the surgeon in order to achieve a proper fit.

Additive manufacturing techniques also allow for the fabrication of even more complex implant designs, including support frames with more robust internal support structures. At the same time, these more robust support structures, which further minimize the risk of plate fracture, can be designed so as to actually use less metal (or other support frame material) compared to support frames fabricated in other ways.

It should be noted that, as used herein, the term "eyelet" means an opening having a substantially closed perimeter, but it is not limited to a particular shape. Thus, the various eyelets described above can be round, square, rectangular, trapezoidal, hexagonal, tear-drop, oval, elliptical or any other suitable shape. Of course, other types of attachment apertures or other fastening points may be used in place of, or in addition to the eyelets.

It will be understood that additional structural supports may be provided on any of the support frames described above, such as additional support girders extending across the width or length of a support frame.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required.

What is claimed is:

1. A bone implant comprising:
   (a) a wire mesh support frame comprising a plurality of interconnected wire members, and at least two fastening points comprising retention eyelets, each of the retention eyelets connected to the support frame by at least one deformable retention arm comprising one of said wire members; and
   (b) a biocompatible plate formed about the support frame, the plate having at least two open cavities therein, said open cavities having a wall;
   wherein each of said retention arms extends out of the plate from or into one of said open cavities such that said retention eyelets are located external to the plate for use in securing the implant to bone, and further wherein said open cavities are configured such that a gap is provided between each of the deformable retention arms and the wall of the open cavity from or into which the deformable retention arm extends, thereby reducing the risk of plate cracking when the retention arms are deformed.

2. The bone implant of claim 1, wherein each of said retention arms extends away from the outer perimeter of the plate such that the retention eyelets are spaced away from the outer perimeter of the plate by the retention arms.

3. The bone implant of claim 2, wherein each of said retention arms extends out of the plate from one of said open cavities, through an aperture having a diameter greater than the diameter of the retention arm.

4. The bone implant of claim 1, wherein the support frame includes at least one wire rim located within the plate, and each of the retention arms is connected to said at least one wire rim.

5. The bone implant of claim 4, wherein portions of the at least one wire rim to which the retention arms are attached are located within said open cavities.

6. The bone implant of claim 5, wherein the support frame includes a plurality of interconnected rims located within the plate, each of said rims traversing a continuous, closed loop.

7. The bone implant of claim 6, wherein each of said retention arms extends away from the outer perimeter of the plate such that the retention eyelets are spaced away from the outer perimeter of the plate by the retention arms.

8. The bone implant of claim 1, wherein said plate has an outer surface and a bone-facing surface, said open cavities are located within the bone-facing surface of the plate, each retention eyelet and its at least one retention arm are located within one of said cavities, and further wherein said plate includes a bore associated with each of said retention eyelets, each of said bores extending through the thickness of the plate and axially aligned with the associated eyelet.

9. The bone implant of claim 8, wherein said support frame comprises an internal rim located inside the plate and having a shape approximating that of the outer perimeter of the plate, and further wherein each of said retention arms extends inwardly from said rim of the support frame into one of said open cavities.

10. The bone implant of claim 8, further comprising a cylindrical sleeve located within each of said bores and spaced away from the eyelet aligned with the bore, wherein each of said cylindrical sleeves is supported by a plurality of support arms that extend upwardly away from the internal rim of the support frame.

11. The bone implant of claim 1, wherein said biocompatible plate comprises a bioceramic material.

12. The bone implant of claim 11, wherein said biocompatible mosaic plates comprise a cement comprising at least 55 wt. % monetite.

13. A method of manufacturing the implant of claim 1, comprising the steps of:
  (a) determining the desired size and shape of the biocompatible plate using a digital representation of at least a portion of a patient's skull;
  (b) fabricating a mold for the biocompatible plate;
  (c) fabricating the wire mesh support frame;
  (d) positioning the support frame within the mold; and
  (e) molding the plate about the support frame.

14. The method of claim 13, further comprising the step of positioning guards over portions of the support frame prior to molding the plate, wherein the guards prevent the formation of plate material at the location of the guards so as to form the open cavities.

15. The bone implant of claim 1, wherein surfaces of said wire mesh support frame are textured.

16. The bone implant of claim 1, wherein said plate has an outer surface and a bone-facing surface, at least one of said open cavities located within the bone-facing surface of the plate.

* * * * *